(12) United States Patent
Kawai et al.

(10) Patent No.: US 8,674,116 B2
(45) Date of Patent: Mar. 18, 2014

(54) METAL COMPLEX AND USE THEREOF

(75) Inventors: Tsuyoshi Kawai, Ikoma (JP);
Yasuchika Hasegawa, Ikoma (JP);
Tetsuya Nakagawa, Ikoma (JP)

(73) Assignees: National University Corporation, Nara (JP); Nara Institute of Science and Technology, Nara (JP)

( * ) Notice: Subject to any disclaimer, the term of this patent is extended or adjusted under 35 U.S.C. 154(b) by 141 days.

(21) Appl. No.: 13/321,204

(22) PCT Filed: May 18, 2010

(86) PCT No.: PCT/JP2010/058360
§ 371 (c)(1),
(2), (4) Date: Nov. 18, 2011

(87) PCT Pub. No.: WO2010/134524
PCT Pub. Date: Nov. 25, 2010

(65) Prior Publication Data
US 2012/0063289 A1 Mar. 15, 2012

(30) Foreign Application Priority Data
May 19, 2009 (JP) ................................. 2009-120950

(51) Int. Cl.
*C07D 333/52* (2006.01)
(52) U.S. Cl.
USPC ............................................................ 549/3
(58) Field of Classification Search
USPC ............................................................ 549/3
See application file for complete search history.

(56) References Cited

U.S. PATENT DOCUMENTS

2009/0163693 A1    6/2009   Kim

FOREIGN PATENT DOCUMENTS

| JP | 7-07774 | 3/1995 |
| JP | 2002-285146 | 10/2002 |
| JP | 2004-039009 | 2/2004 |
| JP | 2009-79132 | 4/2009 |
| WO | WO 2008/04751 | 1/2008 |

OTHER PUBLICATIONS

International Search Report for PCT/JP2010/058360, mailed Jul. 13, 2010.
Yam et al., "Photochromic and Luminescence Switching Properties of a Versatile Diarylethene-Containing 1,10-Phenanthroline Ligand and its Rhenium(I) Complex", *JACS Communications*, vol. 126, Sep. 2004, pp. 12734-12735.
Nakagawa et al., "Synthesis and Emission Properties of Photochromic Eu (III) Complex with Sulfonic Substitutent", *Rare Earths*, No. 54, May 2009, pp. 76-77 (Full Translation).
Chen et al., "Reversible near-infrared fluorescence switch by novel photochromic unsymmertrical-phthalocyanine hybrids based on bisthienylethene", *Chem. Commun.*, Apr. 2002, pp. 1060-1061.
Yutaka et al., "Photochemical Behavior of Azobenzene-Conjugated $Co^{II}$, $Co^{III}$, and $Fe^{II}$ Bis(terpyridine) Complexes", *Inorg. Chem.*, Sep. 2003, pp. 6306-6313.
Nakagawa et al., "Photophysical Properties of Photo-responsive Rare Earth Complex with Photochromic Ligand", *Abstract of annual meeting of photochemistry*, Sep. 2009, p. 162 (Full Translation).

*Primary Examiner* — Brian McDowell
(74) *Attorney, Agent, or Firm* — Nixon & Vanderhye PC

(57) ABSTRACT

There is provided a metal complex that is large in degree of a change in emission intensity, the change being caused by a change in molecular structure of a ligand through a photochromic reaction. The metal complex is arranged such that a diarylethene-based photochromic molecule coordinates to a metal ion via two groups directly bonded to respective reaction site carbons and that the groups are each independently a group selected from Formula Group (1) below.

(1)

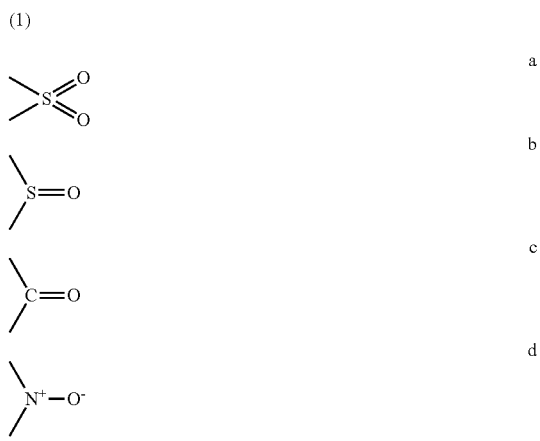

7 Claims, 6 Drawing Sheets

METAL COMPLEX AND USE THEREOF

This application is the U.S. national phase of International Application No. PCT/JP2010/058360 filed 18 May 2010 which designated the U.S. and claims priority to JP Patent Application No. 2009-120950 filed 19 May 2009, the entire contents of each of which are hereby incorporated by reference.

TECHNICAL FIELD

The present invention relates to a metal complex and its use. In particular, the present invention relates to (i) a metal complex in which a photochromic molecule is coordinated and (ii) use of the metal complex.

BACKGROUND ART

There are known a large number of organic molecules each reversibly changing its molecular structure upon light irradiation. Such organic molecules, each of which exhibits a significant color change due to the molecular structure change, are called photochromic molecules.

A photochromic molecule reversibly changes its molecular structure and physicochemical property through a photochemical reaction (also referred to as "photochromic reaction"). There has thus been a lot of research on the photochromic molecule as an optical switching unit that is incorporated in various molecules to cause chemical and physical changes. There has been reported, as such an optical switching unit, a metal complex including a photochromic molecule as a ligand.

In a metal complex, the light emission property of a metal ion depends on symmetry of the metal complex. It is known that in a metal complex including a photochromic molecule as a ligand, a change in molecular structure of the photochromic molecule changes the symmetry of the metal complex and thus changes the light emission property of the metal ion. In other words, irradiating the photochromic molecule in the metal complex with light changes the molecular structure of the photochromic molecule, which in turn changes the light emission property, for example, an emission intensity of the metal ion which emission intensity is observed when the metal ion is excited by exciting light particular for the metal ion. This indicates that a metal complex including a photochromic molecule as a ligand makes it possible to increase and attenuate the emission intensity with use of an optical signal.

An example of a metal complex including a photochromic molecule as a ligand is a complex illustrated in FIG. 6, the complex including, incorporated in phenanthroline as a ligand, diarylethene serving as a photochromic molecule. This complex can undergo an emission color change with use of MLCT transition control of the complex by ON/OFF switching of π conjugated system through a photochromic reaction. The above complex is thus reported to have a possibility in application as a molecular device (see Non Patent Literature 1).

There has also been reported reversible fluorescence switching, as illustrated in FIG. 7, that involves a photochromic site in phthalocyanine and that uses a fluorescence quenching effect caused by a photochromic reaction (see Non Patent Literature 2).

There has further been reported a photochromic property of bis(terpyridine) metal complex conjugated with azobenzene (see Non Patent Literature 3).

There have also been reports, although not on a metal complex including a photochromic molecule as a ligand, but that concern a coloring material and an optical information storage material each including diarylethene serving as a photochromic molecule (see Patent Literatures 1, 2, and 3).

Patent Literature 1 discloses an optical information storage material that, in order to improve stability in information storage and durability for repeated use, includes in a main recording layer including a photochromic composition a pigment which absorbs light at a wavelength longer than an absorption wavelength of a photochromic material that is in a colored state. Patent Literature 2 discloses an optical information storage material that is capable of emitting, for example, brown on its own and that has a high speed of interconversion between tautomers. The respective optical information storage materials of Patent Literatures 1 and 2 each achieve optical recording monomolecularly, and are thus not concerned with a metal complex including a photochromic molecule as a ligand.

Patent Literature 3 attempts to provide a solution to the problem that it is difficult to improve sensitivity of a color dosimeter including a photochromic compound because the color dosimeter transmits radioactive rays. Specifically, Patent Literature 3 discloses a method for effectively introducing in a film a metal serving as a material that does not transmit radioactive rays, in which method a metal complex is present at a particular proportion with respect to the photochromic compound. Patent Literature 3, however, does not intend to utilize a change in the light emission property of a metal ion which change is caused by a coordinate bond of a photochromic molecule to a metal.

CITATION LIST

Patent Literature 1
Japanese Patent Application Publication, Tokukaihei, No. 7-77774 A (Publication Date: Mar. 20, 1995)
Patent Literature 2
Japanese Patent Application Publication, Tokukai, No. 2009-79132 A (Publication Date: Apr. 16, 2009)
Patent Literature 3
Japanese Patent Application Publication, Tokukai, No. 2002-285146 A (Publication Date: Oct. 3, 2002)
Non Patent Literature 1
V. W. W. Yam, C. C. Ko and N.Y. Zhu, J. Am. Chem. Soc., 2004, 126, 12734
Non Patent Literature 2
B. Chen, M. Wang, Y. Wu and He. Tian, Chem. Commun, 2002, 1060
Non Patent Literature 3
Inorg. Chem. 2003, 42, 6306-6313

SUMMARY OF INVENTION

Technical Problem

None of the above conventional techniques, however, purely utilizes a change in light emission property of a metal ion which change is caused by a change in molecular structure of a photochromic molecule. The above conventional techniques are thus problematically insufficient for practical use in various applications such as increasing and attenuating an emission intensity with use of an optical signal.

The present invention has been accomplished in view of the above problem. It is an object of the present invention to provide a metal complex including a photochromic molecule as a ligand, which metal complex is large in degree of a change in light emission property of the metal ion, the change being caused by a change in molecular structure of the ligand through a photochromic reaction.

Solution to Problem

The inventors of the present invention, as a result of diligently studies for the above object, have uniquely found that the arrangement in which a diarylethene-based photochromic molecule coordinates to a metal ion via two particular groups directly bonded to respective reaction site carbons makes it possible to provide a metal complex that is large in degree of a change in light emission property of the metal ion, the change being caused by a change in molecular structure of the ligand through a photochromic reaction. The inventors have consequently made the present invention, which encompasses the subject matter below.

[1] A metal complex in which a diarylethene-based photochromic molecule coordinates to a metal ion, the photochromic molecule coordinating to the metal ion via two groups directly bonded to respective first and second reaction site carbons, the groups being each independently selected from Formula Group (1) below.

(1)

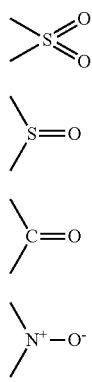

a b c d

[2] The metal complex according to [1], wherein the photochromic molecule is a ligand having a structure represented by General Formula (2) below.

(2)

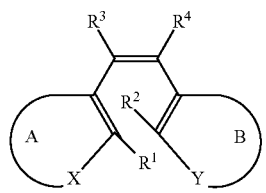

where: the groups X and Y are each independently selected from Formula Group (1) below.

(1)

a

b

c

d $R^1$ and $R^2$ are each independently an alkyl group, an alkoxyl group, a halogen atom, a fluorine-substituted alkyl group, a cyano group, a hydroxyl group, a carboxyl group, or a substituted or unsubstituted aryl group; $R^3$ and $R^4$ either (i) are each independently a hydrogen atom, an alkyl group, an alkoxyl group, a halogen atom, a fluorine-substituted alkyl group, a cyano group, a hydroxyl group, a carboxyl group, or a substituted or unsubstituted aryl group or (ii) together form a substituted or unsubstituted hydrocarbon ring or a substituted or unsubstituted heterocycle; the ring A is a hydrocarbon ring or heterocycle formed by the group X, the first reaction site carbon bonded to the group X, and a carbon atom adjacent to the first reaction site carbon, the hydrocarbon ring or heterocycle either (i) being a monocycle or (ii) forming a condensed ring together with at least one other hydrocarbon ring or heterocycle; and the ring B is a hydrocarbon ring or heterocycle formed by the group Y, the second reaction site carbon bonded to the group Y, and a carbon atom adjacent to the second reaction site carbon, the hydrocarbon ring or heterocycle either (i) being a monocycle or (ii) forming a condensed ring together with at least one other hydrocarbon ring or heterocycle.

[3] The metal complex according to [1] or [2], wherein the photochromic molecule is a ligand having either (I) a structure represented by General Formula (3) below.

(3)

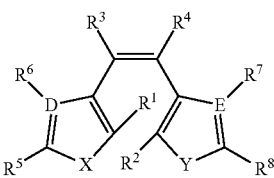

where: the groups X and Y are each independently selected from a, b, and c in Formula Group (1); $R^1$ and $R^2$ are each independently an alkyl group, an alkoxyl group, a halogen atom, a fluorine-substituted alkyl group, a cyano group, a hydroxyl group, a carboxyl group, or a substituted or unsubstituted aryl group; $R^3$ and $R^4$ either (i) are each independently a hydrogen atom, an alkyl group, an alkoxyl group, a halogen atom, a fluorine-substituted alkyl group, a cyano group, a hydroxyl group, a carboxyl group, or a substituted or unsubstituted aryl group or (ii) together form a substituted or unsubstituted hydrocarbon ring or a substituted or unsubstituted heterocycle; D and E are each independently a carbon atom or a nitrogen atom; $R^5$ and $R^6$ either (i) are each independently a hydrogen atom, an alkyl group, an alkoxyl group, a halogen atom, a fluorine-substituted alkyl group, a cyano group, a hydroxyl group, a carboxyl group, or a substituted or unsubstituted aryl group or (ii) together form a substituted or unsubstituted hydrocarbon ring or a substituted or unsubstituted heterocycle; and $R^7$ and $R^8$ either (i) are each independently a hydrogen atom, an alkyl group, an alkoxyl group, a halogen atom, a fluorine-substituted alkyl group, a cyano group, a hydroxyl group, a carboxyl group, or a substituted or unsubstituted aryl group or (ii) together form a substituted or unsubstituted hydrocarbon ring or a substituted or unsubstituted heterocycle; or (II) a structure represented by General Formula (4) below.

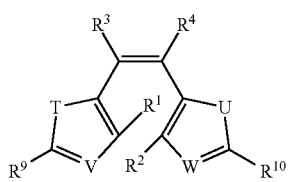

(4)

where: the groups V and W are each independently a group represented by d in Formula Group (1); $R^1$ and $R^2$ are each independently an alkyl group, an alkoxyl group, a halogen atom, a fluorine-substituted alkyl group, a cyano group, a hydroxyl group, a carboxyl group, or a substituted or unsubstituted aryl group; $R^3$ and $R^4$ either (i) are each independently a hydrogen atom, an alkyl group, an alkoxyl group, a halogen atom, a fluorine-substituted alkyl group, a cyano group, a hydroxyl group, a carboxyl group, or a substituted or unsubstituted aryl group or (ii) together form a substituted or unsubstituted hydrocarbon ring or a substituted or unsubstituted heterocycle; T and U are each independently a carbon atom or a sulfur atom; and $R^9$ and $R^{19}$ are each independently a hydrogen atom, an alkyl group, an alkoxyl group, a halogen atom, a fluorine-substituted alkyl group, a cyano group, a hydroxyl group, a carboxyl group, or a substituted or unsubstituted aryl group.

[4] The metal complex according to any one of [1] to [3], wherein the photochromic molecule is a ligand having a structure represented by General Formula (5) below.

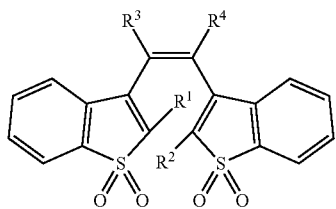

(5)

where: $R^1$ and $R^2$ are each independently an alkyl group, an alkoxyl group, a halogen atom, a fluorine-substituted alkyl group, a cyano group, a hydroxyl group, a carboxyl group, or a substituted or unsubstituted aryl group; and $R^3$ and $R^4$ either (i) are each independently a hydrogen atom, an alkyl group, an alkoxyl group, a halogen atom, a fluorine-substituted alkyl group, a cyano group, a hydroxyl group, a carboxyl group, or a substituted or unsubstituted aryl group or (ii) together form a substituted or unsubstituted hydrocarbon ring or a substituted or unsubstituted heterocycle.

[5] The metal complex according to any one of [1] to [4], wherein a ligand, other than the photochromic molecule, which has a structure selected from General Formula Group (6) below coordinates to the metal ion.

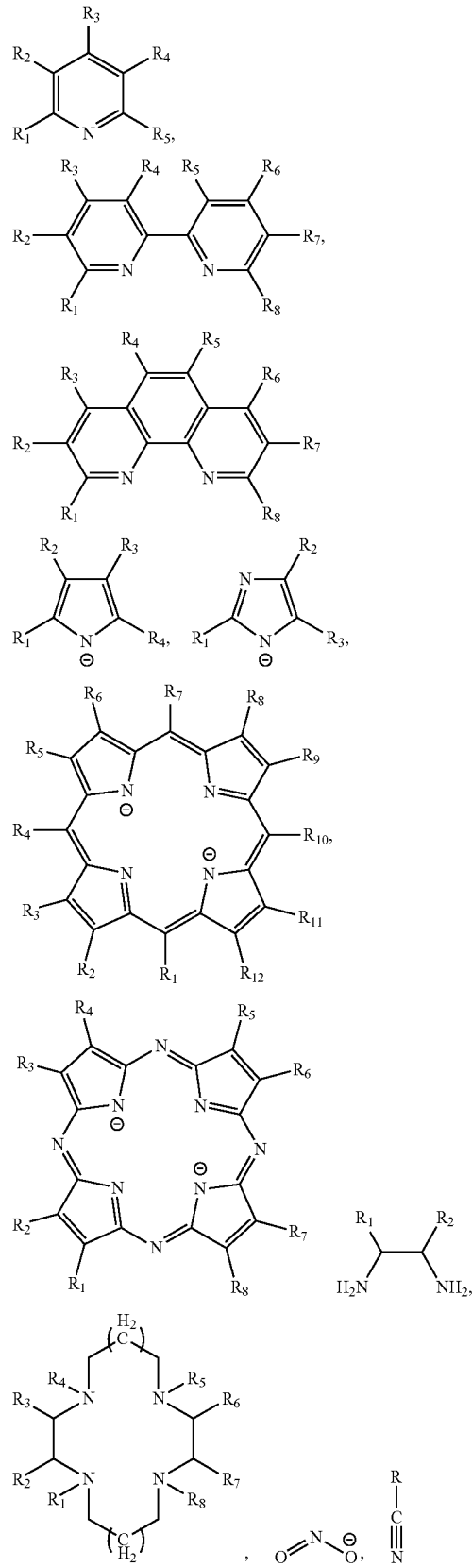

(6)

-continued

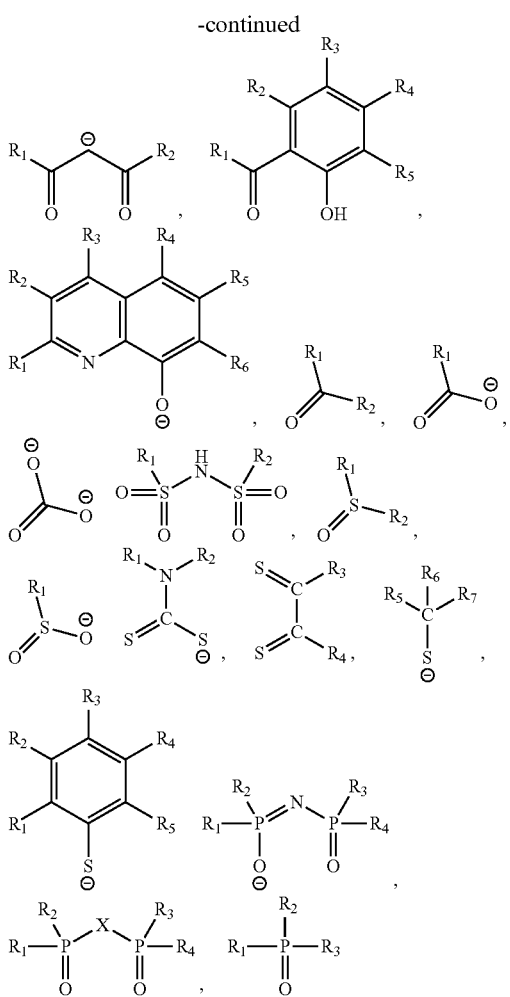

where $R_1$, $R_2$, $R_3$, $R_4$, $R_5$, $R_6$, $R_7$, $R_8$, $R_9$, $R_{10}$, $R_{11}$, and $R_{12}$ are each independently a hydrogen atom, an alkyl group, an alkoxyl group, a halogen atom, a fluorine-substituted alkyl group, a cyano group, a hydroxyl group, a carboxyl group, or a substituted or unsubstituted aryl group.

[6] A metal complex having a structure represented by General Formula (7) below.

(7)

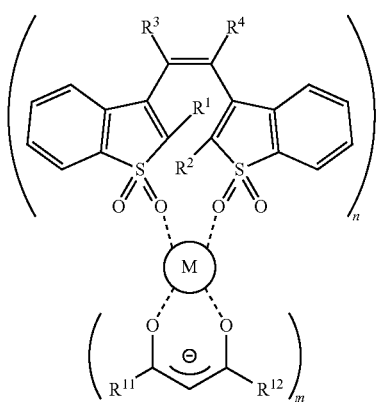

where: $R^1$ and $R^2$ are each independently an alkyl group, an alkoxyl group, a halogen atom, a fluorine-substituted alkyl group, a cyano group, a hydroxyl group, a carboxyl group, or a substituted or unsubstituted aryl group; $R^3$ and $R^4$ either (i) are each independently a hydrogen atom, an alkyl group, an alkoxyl group, a halogen atom, a fluorine-substituted alkyl group, a cyano group, a hydroxyl group, a carboxyl group, or a substituted or unsubstituted aryl group or (ii) together form a substituted or unsubstituted hydrocarbon ring or a substituted or unsubstituted heterocycle; $R^{11}$ and $R^{12}$ are each independently an alkyl group having 1 to 8 carbon atoms, a fluorine-substituted alkyl group having 1 to 8 carbon atoms, or a phenyl group; M represents the metal ion; n is an integer of 1 to 5; m is an integer of 0 to 4; and a sum of n and m is 6 or less.

[7] The metal complex according to any one of [1] to [6], wherein the metal ion is a rare-earth ion.

[8] The metal complex according to [7], wherein the rare-earth ion is a trivalent ion.

[9] The metal complex according to [8], wherein the trivalent ion is one of $Ce^{3+}$, $Nd^{3+}$, $Sm^{3+}$, $Eu^{3+}$, $Tb^{3+}$, $Dy^{3+}$, $Er^{3+}$, $Pr^{3+}$, $Tm^{3+}$, and $Yb^{3+}$.

[10] A composition, including: the metal complex according to any one of [1] to [9]; and a medium.

[11] An information identifying medium, including: the composition according to [9].

[12] An information recording and reproduction method, including the steps of: recording, by irradiating either the metal complex according to any one of [1] to [9] or the composition according to [10] with a light beam having a wavelength $\lambda 1$, information in the photochromic molecule; and reproducing, by (i) irradiating either the metal complex or the composition with a light beam having a wavelength $\lambda 3$, (ii) receiving light emitted by either the metal complex or the composition, and (iii) measuring an emission intensity of the emitted light, the information, which has been stored in the photochromic molecule, on a basis of the measured emission intensity of the emitted light.

[13] The information recording and reproduction method according to [12], further including the step of: erasing, by irradiating either the metal complex or the composition with a light beam having a wavelength $\lambda 2$, the information stored in the photochromic molecule.

[14] An information identifying method, including: a first irradiation step for irradiating either the metal complex according to any one of [1] to [9] or the composition according to [10] with a light beam having a wavelength $\lambda 1$; a first light emission measuring step for (i) irradiating either the metal complex or the composition after the first irradiation step with a light beam having a wavelength $\lambda 3$, (ii) receiving first light emitted by either the metal complex or the composition, and (iii) measuring a first emission spectrum of the first light emitted; a second irradiation step for irradiating either the metal complex or the composition with a light beam having a wavelength $\lambda 2$; a second light emission measuring step for (i) irradiating either the metal complex or the composition after the second irradiation step with a light beam having the wavelength $\lambda 3$, (ii) receiving second light emitted by either the metal complex or the composition, and (iii) measuring a second emission spectrum of the second light emitted; a calculating step for calculating respective intensities of the first and second emission spectra measured during the first and second light emission measuring steps respectively; and an identifying step for identifying identification information associated with a result obtained by the calculating step.

[15] The information identifying method according to [14], wherein the calculating step includes: a first calculating substep for calculating a first ratio of intensities of line spectra having respective particular wavelengths and included in the first emission spectrum measured during the first light emission measuring step; and a second calculating sub-step for calculating a second ratio of intensities of line spectra having the respective particular wavelengths and included in the second emission spectrum measured during the second light emission measuring step, and the identifying step identifies (i) identification information associated with the first ratio calculated during the first calculating sub-step and (ii) identification information associated with the second ratio calculated during the second calculating sub-step.

[16] The information identifying method according to [15], wherein the calculating step includes: a first calculating sub-step for calculating a first ratio of intensities of line spectra having respective particular wavelengths and included in the first emission spectrum measured during the first light emission measuring step; a second calculating sub-step for calculating a second ratio of intensities of line spectra having the respective particular wavelengths and included in the second emission spectrum measured during the second light emission measuring step; and a third calculating sub-step for calculating a third ratio of (i) the first ratio calculated during the first calculating sub-step and (ii) the second ratio calculated during the second calculating sub-step, and the identifying step identifies identification information associated with the third ratio calculated during the third calculating sub-step.

[17] A light intensity adjustment method, including the step of: in a case where either the metal complex according to any one of [1] to [9] or the composition according to [10] has been excited by a light beam having a wavelength λ3, controlling, with use of a light beam having a wavelength λ1 and a light beam having a wavelength λ2, an emission intensity of light emitted by either the metal complex or the composition.

Advantageous Effects of Invention

The metal complex of the present invention is, as described above, arranged such that the diarylethene-based photochromic molecule coordinates to the metal ion via two groups directly bonded to respective reaction site carbons and that the groups are each independently a group selected from Formula Group (1) above. This arrangement makes it possible to provide a metal complex including a photochromic molecule as a ligand, which metal complex is large in degree of a change in light emission property of the metal ion, the change being caused by a change in molecular structure of the ligand through a photochromic reaction. The above arrangement thus makes it possible to (i) increase and attenuate an emission intensity with use of an optical signal and consequently to (ii) provide a highly sensitive light switching unit.

Figure 1:
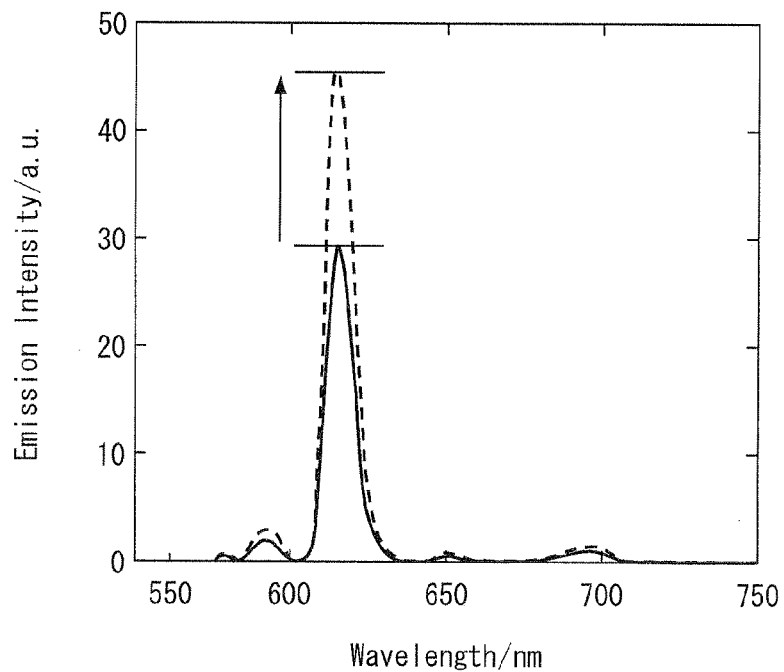
FIG. 1 is a graph indicative of an emission spectrum of [Eu(BTFO4)(HFA)$_3$] in accordance with an embodiment of the present invention.

DESCRIPTION OF EMBODIMENTS (I) Metal Complex of the Present Invention

Attaining the above object, that is, increasing a change caused in light emission property of a metal complex by a change in molecular structure of a ligand, presumably simply requires increasing such a change in molecular structure. According to common general technical knowledge of the field, increasing a change in molecular structure of a ligand should importantly involve use of a photochromic molecule that undergoes a large change in molecular structure near a reaction center (in a diarylethene-based photochromic molecule, carbons that are present at two reaction sites and involved in a ring-closing/ring-opening reaction) of a photochromic reaction.

The inventors of the present invention have, as a result of constant studies from their unique viewpoint, found that an emission intensity and its change due to a structural change in a ligand are significantly large in a case where the ligand is a diarylethene-based photochromic molecule, two particular groups are directly bonded to respective reaction site carbons, and the ligand is coordinated to a metal ion via the particular groups.

According to the common general technical knowledge, it is not easy to assume that a binding site of a ligand to a metal ion influences a change in light emission property of a metal complex. The inventors' unique viewpoint is thus not something that those skilled in the art can easily arrive at.

Further, a metal ion present near a photochromic molecule typically tends to sterically prevent a structural change in the photochromic molecule, and thus presumably decreases its photochromic reactivity. A reaction center and a metal ion located closely to each other are thus presumably not preferable. According to the present invention based on a new knowledge, however, a metal ion is located very closely to reaction site carbons of a photochromic molecule, but such a close location does not decrease reactivity of the photochromic molecule. Such a further advantage of the present invention is not something that those skilled in the art can expect.

Specifically, a metal complex of the present invention is a metal complex in which a diarylethene-based photochromic molecule coordinates to a metal ion, the photochromic molecule coordinating to the metal ion via two groups directly bonded to respective first and second reaction site carbons, the groups being each independently selected from Formula Group (1) below.

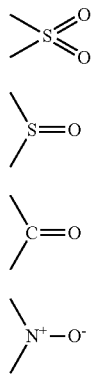

(1)

a b c d

In the description of the present invention, the term "photochromic molecule" refers to a molecule having photochromic reactivity. The term "photochromic reactivity" refers to a property of a chemical species, with which property a single chemical species reversibly changes, due to action of light, into two different isomers with different absorption spectra through rearrangement of chemical bonding without changing a molecular weight of the chemical species. The two isomers of the photochromic molecule, which differ from each other in molecular structure, thus differ from each other in various molecule physical properties including not only absorption spectrum but also fluorescence property, refractive index, and dipole moment.

In the description of the present invention, the term "diarylethene-based photochromic molecule" refers to a diarylethene-based photochromic molecule that undergoes a ring-closing/ring-opening reaction due to action of light and that includes two reaction site carbons involved in the ring-closing/ring-opening reaction.

More specifically, a diarylethene-based photochromic molecule causes a ring-closing reaction between two reaction site carbons upon irradiation of a light beam having a particular wavelength λ1, and thus changes from an opened-ring form to a closed-ring form. A diarylethene-based photochromic molecule then causes a ring-opening reaction between the two reaction site carbons upon irradiation of a light beam having a particular wavelength λ2 different from the wavelength λ1, and thus changes from the closed-ring form back to the original opened-ring form. The wavelengths λ1 and λ2, which differ from each other, are particular for the photochromic molecule. As described above, in the metal complex of the present invention, the molecular structure of the diarylethene-based photochromic molecule can be reversibly changed between a closed-ring form and an opened-ring form with use of a light beam having the wavelength λ1 and a light beam having the wavelength λ2.

A diarylethene compound is advantageously high in thermal irreversibility, storage stability under a light-blocking condition, and durability in repeated use.

In the description of the present invention, the term "reaction site carbons" refers to two carbon atoms involved in a ring-closing/ring-opening reaction caused by action of light. Further, the two carbon atoms become bonded to each other in a ring-closing reaction, whereas the bond between the two carbon atoms is ring-opened in a ring-opening reaction.

In the metal complex of the present invention, the diarylethene-based photochromic molecule coordinates to the metal ion via two groups directly bonded to respective first and second reaction site carbons, the groups being each independently selected from Formula Group (1) above. Specifically, in the case where the groups are each either a or b, the photochromic molecule coordinates to the metal atom via a sulfur atom and an oxygen atom; in the case where the groups are each c, the photochromic molecule coordinates to the metal atom via a carbon atom and an oxygen atom; and in the case where the groups are each d, the photochromic molecule coordinates to the metal atom via a nitrogen atom and an oxygen atom.

The metal complex of the present invention has a structure in which a diarylethene-based photochromic molecule is coordinated to a metal ion. The photochromic molecule bonded to the metal ion may be replaced by a ligand (hereinafter referred to as "other ligand") other than the photochromic molecule. The following describes in detail the metal complex of the present invention sequentially through "(I-1) Photochromic Molecule", "(I-2) Metal Ion", "(I-3) Other ligands", and "(I-4) Properties of the metal complex of the Present Invention".

(I-1) Photochromic Molecule

The photochromic molecule is not particularly limited as long as it is a diarylethene-based photochromic molecule that can coordinate to a metal ion via two groups of a kind selected from Formula Group (1) above, the two groups being directly bonded to respective reaction site carbons. A suitable example of the photochromic molecule is a photochromic molecule having a structure represented by General Formula (2) below.

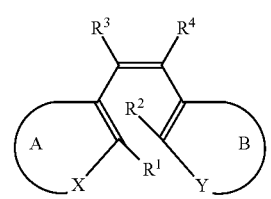

(2)

In General Formula (2) above, the groups X and Y are each independently a group selected from Formula Group (1) above. The photochromic molecule is coordinated to a metal ion via the groups X and Y.

In General Formula (2) above, $R^1$ and $R^2$ are each independently an alkyl group, an alkoxyl group, a halogen atom, a fluorine-substituted alkyl group, a cyano group, a hydroxyl group, a carboxyl group, or a substituted or unsubstituted aryl group. The above alkyl group is preferably a linear or branched alkyl group having 1 to 20 carbon atoms. Specific examples of such an alkyl group include a methyl group, an ethyl group, a propyl group, an isopropyl group, a butyl group, an isobutyl group, a sec-butyl group, a tert-butyl group, a pentyl group, a hexyl group and the like. The above alkoxyl group is preferably a linear or branched alkoxyl group having 1 to 20 carbon atoms. Specific examples of such an alkoxyl group include a methoxy group, an ethoxy group, a propoxyl group, an isopropoxyl group, a butoxy group, an isobutoxy group, a sec-butoxy group, a tert-butoxy group, a pentyloxy group, a pentyloxy group and the like. The above halogen atom is, for example, a fluorine atom, a chlorine atom, a bromine atom, or an iodine atom. The above fluorine-substituted alkyl group is preferably a group formed by the above alkyl group with at least one hydrogen atom substituted by a fluorine atom. Suitable examples of such a group include a trifluoromethyl group and a pentafluoroethyl group. The above aryl group is not particularly limited. Preferable examples of it include a phenyl group, a biphenyl group, a naphthyl group, a pyridyl group, and a thienyl group. In the case where the aryl group is substituted, examples of a substituent group include an alkyl group, an alkoxyl group, a halogen atom, a fluorine-substituted alkyl group, a cyano group, a hydroxyl group, and a carboxyl group.

In General Formula (2) above, $R^3$ and $R^4$ are each independently a hydrogen atom, an alkyl group, an alkoxyl group, a halogen atom, a fluorine-substituted alkyl group, a cyano group, a hydroxyl group, a carboxyl group, or a substituted or unsubstituted aryl group. Alternatively, $R^3$ and $R^4$ together form a substituted or unsubstituted hydrocarbon ring or a substituted or unsubstituted heterocycle. The alkyl group, the alkoxyl group, the halogen atom, the fluorine-substituted alkyl group, and the substituted or unsubstituted aryl group are as described for $R^1$ and $R^2$ above, and are thus not described here. $R^3$ and $R^4$ may alternatively be bonded to each other via a divalent group (L) to form a substituted or unsubstituted hydrocarbon ring or a substituted or unsubstituted heterocycle. The hydrocarbon ring or heterocycle is preferably a ring such as a five-membered ring, a six-membered ring, a seven-membered ring, and an eight-membered ring, and may or may not be aromatic. The divalent group for forming the hydrocarbon ring (—$R^3$-(L)-$R^4$—) is preferably a saturated or unsaturated hydrocarbon group having 1 to 20 carbon atoms. Specific examples of the divalent group (—$R^3$-(L)-$R^4$—) include a propylene group, a tetramethylene group, a hexamethylene group, a heptamethylene group, a pentenylene group, a hexenylene group, and a heptenylene group. The divalent group for forming the heterocycle (—$R^3$-(L)-$R^4$—) is, for example, a group formed by the above hydrocarbon group with at least one carbon atom each independently substituted by an atom such as a nitrogen atom, an oxygen atom, a sulfur atom, a phosphorus atom, a silicon atom, and a boron atom. In the case where the hydrocarbon ring or heterocycle is substituted, examples of a substituent group include an alkyl group, an alkoxyl group, a halogen atom, a fluorine-substituted alkyl group, a cyano group, a hydroxyl group, and a carboxyl group. The divalent group for forming the substituted hydrocarbon ring or substituted heterocycle (—$R^3$-(L)-$R^4$—) is not particularly limited as long as it includes the above substituent group. The divalent group may be, for example, a fluorine-substituted alkylene group such as —$(CF_2)n$— (where n is an integer of 3 to 20).

In General Formula (2) above, the ring A represents a hydrocarbon ring or heterocycle formed with the group X, a reaction site carbon bonded to the group X, and a carbon atom adjacent to the reaction site carbon. The hydrocarbon ring or heterocycle is monocyclic or forms a condensed ring together with one or more other hydrocarbon rings or heterocycles, respectively. The hydrocarbon ring or heterocycle each formed with the group X, a reaction site carbon bonded to the group X, and a carbon atom adjacent to the reaction site carbon is not particularly limited as long as it includes a group a, b, c, or d above. The hydrocarbon ring or heterocycle is preferably a five- or six-membered aromatic ring. Examples of the hydrocarbon ring or heterocycle include a benzene ring, a thiophene ring, a pyrrole ring, an imidazole ring, a pyrazole ring, an isothiazole ring, an isoxazole ring, a pyridine ring, a pyrazine ring, a pyrimidine ring, and a pyridazine ring. In the case where the hydrocarbon ring or heterocycle forms a condensed ring together with one or more other hydrocarbon rings or heterocycles respectively, the one or more other hydrocarbon rings or heterocycles are not particularly limited, either. The one or more other hydrocarbon rings or heterocycles may each be a monocycle or a condensed ring. Examples of the one or more other hydrocarbon rings or heterocycles include a benzene ring, a naphthalene ring, an anthracene ring, a thiophene ring, a pyrrole ring, an imidazole ring, a pyrazole ring, an isothiazole ring, an isoxazole ring, a pyridine ring, a pyrazine ring, a pyrimidine ring, and a pyridazine ring.

In General Formula (2) above, the ring B represents a hydrocarbon ring or heterocycle each formed with the group Y a reaction site carbon bonded to the group Y, and a carbon atom adjacent to the reaction site carbon. The hydrocarbon ring or heterocycle is monocyclic or forms a condensed ring together with one or more other hydrocarbon rings or heterocycles, respectively. The hydrocarbon ring or heterocycle each formed with the group Y, a reaction site carbon bonded to the group Y, and a carbon atom adjacent to the reaction site carbon is as described for the ring A, and is thus not described here. Further, the one or more hydrocarbon rings or heterocycles for the case in which the hydrocarbon ring or heterocycle forms a condensed ring therewith are as described for the ring A, and are thus not described here.

A suitable example of the above photochromic molecule is a ligand having a structure represented by General Formula (3) below.

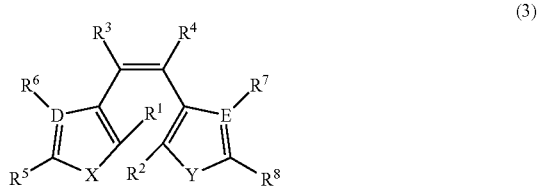

(3)

In General Formula (3), the groups X and Y are each independently a group a, b, or c selected from Formula Group (1) above.

In General Formula (3), D and E are each independently a carbon atom or a nitrogen atom. $R^5$ and $R^6$ are each independently a hydrogen atom, an alkyl group, an alkoxyl group, a halogen atom, a fluorine-substituted alkyl group, a cyano group, a hydroxyl group, a carboxyl group, or a substituted or unsubstituted aryl group. Alternatively, $R^5$ and $R^6$ together form a substituted or unsubstituted hydrocarbon ring or a substituted or unsubstituted heterocycle. $R^7$ and $R^8$ are each independently a hydrogen atom, an alkyl group, an alkoxyl group, a halogen atom, a fluorine-substituted alkyl group, a cyano group, a hydroxyl group, a carboxyl group, or a substituted or unsubstituted aryl group. Alternatively, $R^7$ and $R^8$ together form a substituted or unsubstituted hydrocarbon ring or a substituted or unsubstituted heterocycle.

The alkyl group, the alkoxyl group, the halogen atom, the fluorine-substituted alkyl group, and the substituted or unsubstituted aryl group are as described for $R^1$ and $R^2$.

In General Formula (3), (i) the substituted or unsubstituted hydrocarbon ring or substituted or unsubstituted heterocycle formed by $R^5$ and $R^6$ and (ii) the substituted or unsubstituted hydrocarbon ring or substituted or unsubstituted heterocycle formed by $R^7$ and $R^8$ are not particularly limited, and may each be a monocycle or a condensed ring. Examples include a benzene ring, a naphthalene ring, an anthracene ring, a thiophene ring, a pyrrole ring, an imidazole ring, a pyrazole ring, an isothiazole ring, an isoxazole ring, a pyridine ring, a pyrazine ring, a pyrimidine ring, and a pyridazine ring.

In General Formula (3), $R^1$, $R^2$, $R^3$, and $R^4$ are as described for General Formula (2) above, and are thus not described here.

Another suitable example of the above photochromic molecule is a ligand having a structure represented by General Formula (4) below.

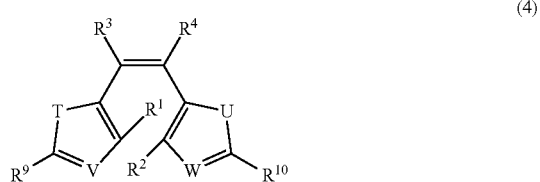

In General Formula (4), the groups V and W are each independently a group represented by d in Formula Group (1) above.

In General Formula (4), T and U are each independently a carbon atom or a sulfur atom, and $R^9$ and $R^{19}$ are each independently a hydrogen atom, an alkyl group, an alkoxyl group, a halogen atom, a fluorine-substituted alkyl group, a cyano group, a hydroxyl group, a carboxyl group, or a substituted or unsubstituted aryl group.

The alkyl group, the alkoxyl group, the halogen atom, the fluorine-substituted alkyl group, and the substituted or unsubstituted aryl group are as described for $R^1$ and $R^2$.

In General Formula (4), $R^1$, $R^2$, $R^3$, and $R^4$ are as described for General Formula (2) above, and are thus not described here.

A more specific, suitable example of the above photochromic molecule is a photochromic molecule having a structure represented by General Formula (5) below.

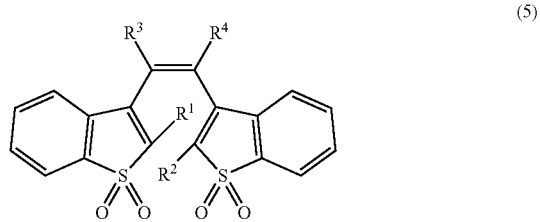

General Formula (5), $R^1$ and $R^2$ are each independently an alkyl group, an alkoxyl group, a halogen atom, a fluorine-substituted alkyl group, a cyano group, a hydroxyl group, a carboxyl group, or a substituted or unsubstituted aryl group. $R^3$ and $R^4$ are each independently a hydrogen atom, an alkyl group, an alkoxyl group, a halogen atom, a fluorine-substituted alkyl group, a cyano group, a hydroxyl group, a carboxyl group, or a substituted or unsubstituted aryl group. Alternatively, $R^3$ and $R^4$ together form a substituted or unsubstituted hydrocarbon ring or a substituted or unsubstituted heterocycle.

$R^1$, $R^2$, $R^3$, and $R^4$ are as described for General Formula (2) above, and are thus not described here.

In the metal complex of the present invention, how many of the photochromic molecule coordinate to the metal ion is not particularly limited. The metal complex may be arranged such that only one photochromic molecule described above is coordinated to the metal ion or that a plurality of the photochromic molecule are coordinated to the metal ion.

In the case where a plurality of the photochromic molecule are coordinated to a metal ion, such a plurality of the photochromic molecule may be identical to one another in kind or may a combination of photochromic molecules different from one another in kind.

(I-2) Metal Ion

The metal ion for use in the metal complex of the present invention is not particularly limited. Examples of the metal ion include: Group 1A elements in the periodic table (Li, Na, K, Rb, Cs, and Fr); Group 2A elements (Be, Mg, Ca, Sr, Ba, and Ra); Group 3A elements (Sc and Y); Group 4A elements (Ti, Zr, and Hf); Group 5A elements (V, Nb, and Ta); Group 6A elements (Cr, Mo, and W); Group 7A elements (Mn, Tc, and Re); Group 8 elements (Fe, Ru, Os, Co, Rh, Ir, Ni, Pd, and Pt); Group 1B elements (Cu, Ag, and Au); Group 2B elements (Zn, Cd, and Hg); a Group 3B element (Al); lanthanoids (La, Ce, Pr, Nd, Pm, Sm, Eu, Gd, Tb, Dy, Ho, Er, Tm, Yb, and Lu); and actinoids (Ac, Th, Pa, U, Np, Pu, Am, Cm, Bk, Cf, Es, Fm, Md, No, and Lr). Thus, coordinating the above diarylethene-based photochromic molecule to any metal ion provides a metal complex which is large in degree of a change caused in light emission property of the metal ion by a change in molecular structure of the photochromic molecule.

The inventors of the present invention have suggested before (i) a complex formed by a combination of a photochromic molecule and a rare-earth metal and (ii) use of the complex. The present invention is, of course, applicable to such a complex as well. Rare-earth ions are advantageous in that (i) some of them emit light within a wide range of wavelengths from ultraviolet light to infrared light, (ii) they are each extremely narrow in wavelength width of a light emission band, (iii) they are high in color purity, and (iv) they are superior in stability in terms of heat, light, and excitation.

Rare-earth ions include Group 3A elements (Sc and Y) and lanthanoids (La, Ce, Pr, Nd, Pm, Sm, Eu, Gd, Tb, Dy, Ho, Er, Tm, Yb, and Lu). Among these, trivalent lanthanoid ions are preferable because in the techniques that the inventors have suggested before, trivalent lanthanoid ions each emit light having a higher intensity than other lanthanoid ions. The present invention is also applicable to such techniques to produce the same effect. Thus, the present invention, in the case where it uses a rare-earth ion, preferably uses a trivalent lanthanoid ion because it emits light having a higher intensity. Particularly preferable among trivalent lanthanoid ions are $Ce^{3+}$, $Nd^{3+}$, $Sm^{3+}$, $Eu^{3+}$, $Tb^{3+}$, $Dy^{3+}$, $Er^{3+}$, $Pr^{3+}$, $Tm^{3+}$, and $Yb^{3+}$.

In the metal complex of the present invention, changing the kind of the metal ion can change the excitation wavelengths, emission intensity, and emission wavelengths of the metal complex. Such excitation wavelengths, emission intensity, and emission wavelengths of the metal complex of the present invention can also be changed by changing, for example, (i) the kind of the photochromic molecule or (ii) the combination of the metal ion and the photochromic molecule.

(I-3) Other Ligands

The metal complex of the present invention may be arranged such that a ligand other than the above photochromic molecule is coordinated to the metal ion. Specific examples of such a ligand include: pyridine and a derivative thereof; a nitrogen-containing heterocycle other than pyridine and a derivative thereof; ethylenediamine, nitro, cyano, and a derivative thereof; a ketone and a derivative thereof; a sulfonyl and a derivative thereof; a thio compound and a derivative thereof; and phosphine oxide and a derivative thereof.

The above pyridine and a derivative thereof are, for example, a ligand represented by any formula selected from General Formula Group (9) below.

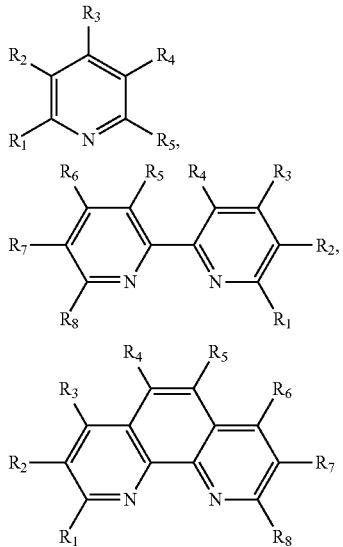
(9)

In General Formula Group (9), $R_1$, $R_2$, $R_3$, $R_4$, $R_5$, $R_6$, $R_7$, and $R_8$ are each independently an alkyl group, an alkoxyl group, a halogen atom, a trifluoromethyl group, a fluorine-substituted alkyl group, a cyano group, a hydroxyl group, a carboxyl group, a sulfonyl group, an aryl group, or a substituted aryl group. Alternatively, $R_1$, $R_2$, $R_3$, $R_4$, $R_5$, $R_6$, $R_7$, and $R_8$ form, with adjacent substituent groups linked to each other, a carbocyclic ring, a heterocycle, a substituted carbocyclic ring, or a substituted heterocycle.

The above nitrogen-containing heterocycle other than pyridine and a derivative thereof are, for example, a ligand represented by any formula selected from General Formula Group (10) below.

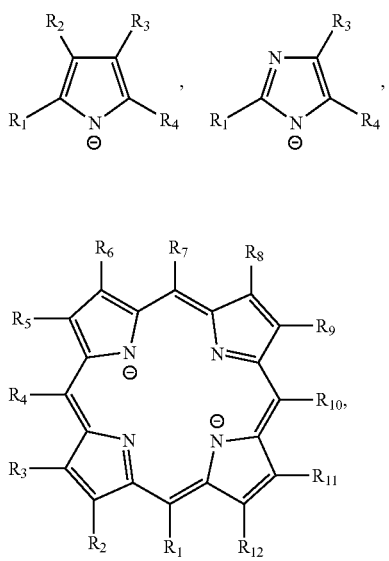
(10)

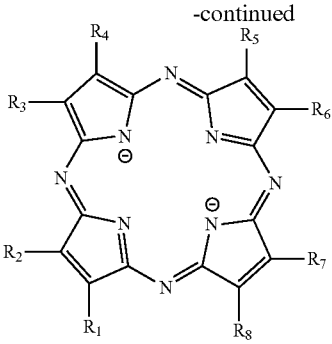
-continued

In General Formula Group (10), $R_1$, $R_2$, $R_3$, $R_4$, $R_5$, $R_6$, $R_7$, $R_8$, $R_9$, $R_{10}$, $R_{11}$, and $R_{12}$ are each independently an alkyl group, an alkoxyl group, a halogen atom, a trifluoromethyl group, a fluorine-substituted alkyl group, a cyano group, a hydroxyl group, a carboxyl group, a sulfonyl group, an aryl group, or a substituted aryl group. Alternatively, $R_1$, $R_2$, $R_3$, $R_4$, $R_5$, $R_6$, $R_7$, $R_8$, $R_9$, $R_{10}$, $R_{11}$, and $R_{12}$ form, with adjacent substituent groups linked to each other, a carbocyclic ring, a heterocycle, a substituted carbocyclic ring, or a substituted heterocycle.

The above ethylenediamine, nitro, cyano, and a derivative thereof are, for example, a ligand represented by any formula selected from General Formula Group (11) below.

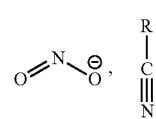
(11)

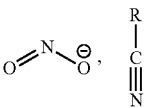

In General Formula Group (11), $R_1$, $R_2$, $R_3$, $R_4$, $R_5$, $R_6$, $R_7$, and $R_8$ are each independently an alkyl group, an alkoxyl group, a halogen atom, a trifluoromethyl group, a fluorine-substituted alkyl group, a cyano group, a hydroxyl group, a carboxyl group, a sulfonyl group, an aryl group, or a substituted aryl group. Alternatively, $R_1$, $R_2$, $R_3$, $R_4$, $R_5$, $R_6$, $R_7$, and $R_8$ form, with adjacent substituent groups linked to each other, a carbocyclic ring, a heterocycle, a substituted carbocyclic ring, or a substituted heterocycle.

The above ketone and a derivative thereof are, for example, a ligand represented by any formula selected from General Formula Group (12) below.

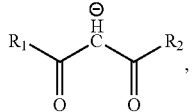
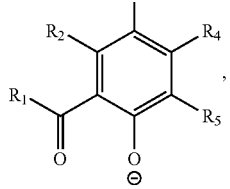
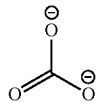
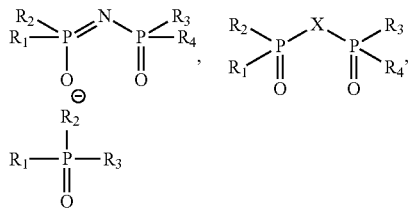

In General Formula Group (14), $R_1$, $R_2$, $R_3$, $R_4$, and $R_5$ are each independently an alkyl group having 1 to 8 carbon atoms, a fluorine-substituted alkyl group having 1 to 8 carbon atoms, or a phenyl group.

The above phosphine oxide and a derivative thereof are, for example, a ligand represented by any formula selected from General Formula Group (15) below.

In General Formula Group (12), $R_1$, $R_2$, $R_3$, $R_4$, $R_5$, and $R_6$ are each independently an alkyl group, an alkoxyl group, a halogen atom, a trifluoromethyl group, a fluorine-substituted alkyl group, a cyano group, a hydroxyl group, a carboxyl group, a sulfonyl group, an aryl group, or a substituted aryl group. Alternatively, $R_1$, $R_2$, $R_3$, $R_4$, $R_5$, and $R_6$ form, with adjacent substituent groups linked to each other, a carbocyclic ring, a heterocycle, a substituted carbocyclic ring, or a substituted heterocycle.

The above sulfonyl and a derivative thereof are, for example, a ligand represented by any formula selected from General Formula Group (13) below.

In General Formula Group (15), $R_1$, $R_2$, $R_3$, and $R_4$ are each independently an alkyl group having 1 to 8 carbon atoms, a fluorine-substituted alkyl group having 1 to 8 carbon atoms, or a phenyl group.

Coordinating any of the above other ligands to a metal ion allows the metal complex of the present invention to, for example, be synthesized easily, be soluble in a solvent, and be more stable.

The metal complex of the present invention, in which any of the above photochromic molecule and the other ligands is coordinated to a metal ion, is for example, a metal complex having a structure represented by General Formula (7) below.

In General Formula Group (13), $R_1$ and $R_2$ are each independently an alkyl group having 1 to 8 carbon atoms, a fluorine-substituted alkyl group having 1 to 8 carbon atoms, or a phenyl group.

The above thio compound and a derivative thereof are, for example, a ligand represented by any formula selected from General Formula Group (14) below.

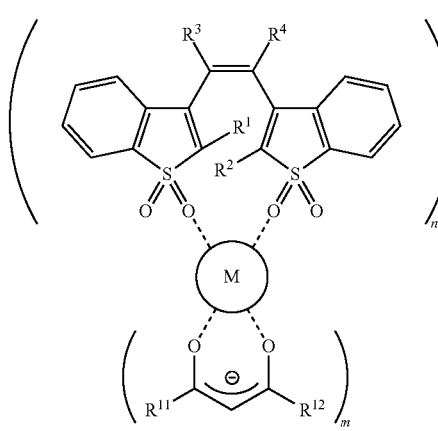

In General Formula (7) above, $R^1$, $R^2$, $R^3$, and $R^4$ are as described for General Formula (2) above, and are thus not described here.

In General Formula (7), $R^{11}$ and $R^{12}$ are each independently an alkyl group having 1 to 8 carbon atoms, a fluorine-substituted alkyl group having 1 to 8 carbon atoms, or a phenyl group. The alkyl group having 1 to 8 carbon atoms may be linear or branched. The fluorine-substituted alkyl group having 1 to 8 carbon atoms is not particularly limited, either. Suitable examples of it include a perfluoroalkyl group such as a perfluoromethyl group, a perfluoroethyl group, a perfluoropropyl group, a perfluorobutyl group, a perfluoropentyl group, a perfluorohexyl group, a perfluoropeptyl group, and a perfluorooctyl group.

In General Formula (7), M is a metal ion, and n is an integer of 1 to 5. In the case where n is an integer of 1 to 5, the present invention preferably achieves its advantages in an effective manner. Further, m is an integer of 0 to 4. In the case where m is an integer of 0 to 4, the ligand can preferably coordinate to a metal ion having a valence of zero to four. In addition, the sum of n and m is preferably six or less. In the case where the sum of n and m is six or less, the metal complex is preferably not larger than dodecacoordinate in coordination structure.

How to produce the above-described metal complex of the present invention is not particularly limited. Producing the metal complex simply requires appropriately selecting, depending on the ligand to be coordinated in the metal complex, preferable methods from among methods that have been publicly known and thus combining such methods.

(I-4) Properties of the Metal Complex of the Present Invention

<Light Emission Property of the Metal Complex of the Present Invention>

The metal complex of the present invention is, when irradiated with a light beam having a particular wavelength excited to emit light. Further, the metal ion of the metal complex has a light emission property that varies according to the molecular structure of the photochromic molecule, that is, whether the photochromic molecule has an opened-ring form or a closed-ring form. Thus, in the metal complex of the present invention, the metal ion has a light emission property, exhibited when the metal complex is excited by a light beam having the wavelength $\lambda 3$, that varies between (i) after the metal complex has been irradiated with a light beam having a wavelength $\lambda 1$ and (ii) after the metal complex has been irradiated with a light beam having a wavelength $\lambda 2$.

In the present specification, the description of the light emission property varying means that the property of a component of emitted light varies, that is, the parity of such a component varies. For example, the expression "the light emission property of a metal ion varies" means that an emission intensity of electric dipole transition varies, the emission intensity being relative to an emission intensity of magnetic dipole transition.

The metal complex of the present invention, which has the above arrangement, has a light emission property of the metal ion which light emission property is due to a structural change in the ligand; particularly, the metal complex has a property by which the emission intensity of the metal ion and a change in the emission intensity are significantly large. The light emission property of the metal ion which light emission property is changed by a structural change in the ligand is not limited to the emission intensity. The light emission property also includes a light emission quantum yield, a light emission duration, and a radiation rate constant calculated from the light emission quantum yield and the light emission duration.

With use of the above property of the metal complex of the present invention, evaluating the light emission property exhibited when the metal ion is irradiated with a light beam having the wavelength $\lambda 3$ makes it possible to determine, with high sensitivity, whether the metal complex of the present invention has a structure for the case in which it has been irradiated with a light beam having the wavelength $\lambda 1$ or a structure for the case in which it has been irradiated with a light beam having the wavelength $\lambda 2$.

The metal complex of the present invention has an emission intensity exhibited when it is excited by a light beam having the wavelength $\lambda 3$, the emission intensity greatly varying depending on whether the metal complex has been irradiated with a light beam having the wavelength $\lambda 1$ or with a light beam having the wavelength $\lambda 2$. This indicates that the metal complex of the present invention is capable of amplifying and attenuating light with use of light. The metal complex of the present invention is thus usable in a control system for an optical amplification device serving as a high-speed switch.

<Absorption Property and Nondestructive Readout of the Metal Complex of the Present Invention>

The photochromic molecule in the metal complex of the present invention changes its molecular structure depending on whether a light beam irradiating the photochromic molecule has the wavelength $\lambda 1$ or the wavelength $\lambda 2$. This change in the molecular structure causes the photochromic molecule to have different absorption bands for respective wavelengths. The inventors have measured absorption spectra exhibited when the molecular structure of the photochromic molecule in the metal complex of the present invention has been changed reversibly by irradiation of a light beam having the wavelength $\lambda 1$ and a light beam having the wavelength $\lambda 2$, and have consequently obtained an unexpected result: The inventors have found that the metal complex, with either of the different molecular structures, has an absorption band at wavelengths shorter than that of exciting light for the metal ion.

This unexpected result indicates that with use of the metal complex of the present invention, utilizing the difference between optical properties of the two isomers and the reversible change between the two isomers advantageously enables nondestructive readout, which has been an object to achieve in the technique of using a photochromic molecule in an optical memory.

A photochromic molecule has different absorption bands for respective wavelengths (colors) due to a change caused in its molecular structure by light irradiation. This color change is applicable as "optical write information." Reading such a color change at a high speed with use of light requires "readout light" for detecting the color. Emitting such "readout light" onto a photochromic molecule having a changed molecular structure, however, causes the photochromic molecule to return to its original chemical structure that the photochromic molecule had before irradiation of "write light," and has thus had a disadvantage that optical information of the photochromic molecule (that is, a change caused by light in the molecular structure) is lost. Although there has been active research on "nondestructive readout" for preventing destruction of such optical information, no practical "nondestructive readout" has been achieved yet.

Figure 8:
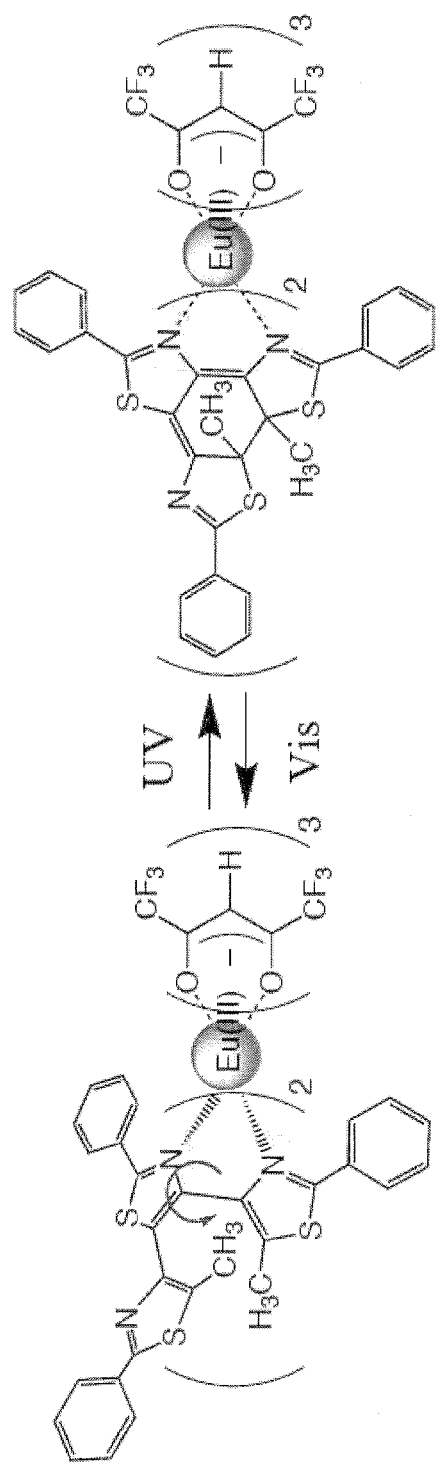
FIG. 8 is a diagram illustrating a conventional metal complex in which a photochromic molecule coordinates to Eu.
Figure 9:
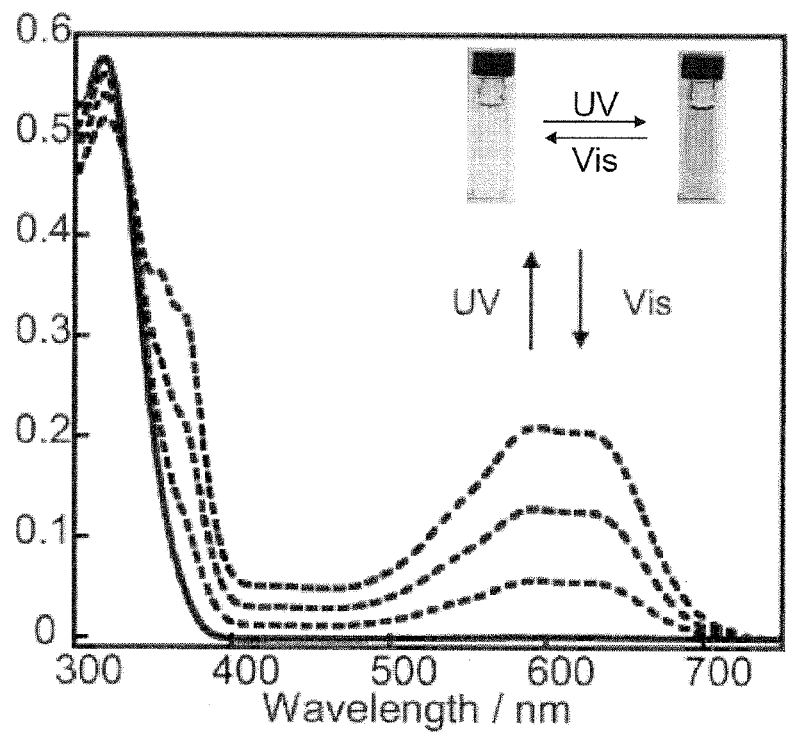
FIG. 9 is a graph illustrating an absorption spectrum of a conventional metal complex in which a photochromic molecule coordinates to Eu.

To solve the problem, the inventors of the present invention have suggested a "photochromic rare earth complex" illustrated in FIG. 8, which combines a photochromic molecule with a rare earth complex. The photochromic rare earth complex, however, when it has changed from an opened-ring form to a closed-ring form due to UV radiation, has an absorption band (that is, an absorption band that the photochromic molecule has due to optical write) of around 600 nm as illustrated in FIG. 9. This absorption band unfortunately coincides with readout wavelengths and emission wavelengths of Eu(III). Thus, irradiating the photochromic rare earth complex with "readout light" causes the photochromic rare earth complex to return to the chemical form (opened-ring form) that the photochromic rare earth complex had before irradiation of "write light." Perfect nondestructive readout, in consequence, remained to be achieved.

Figure 5:
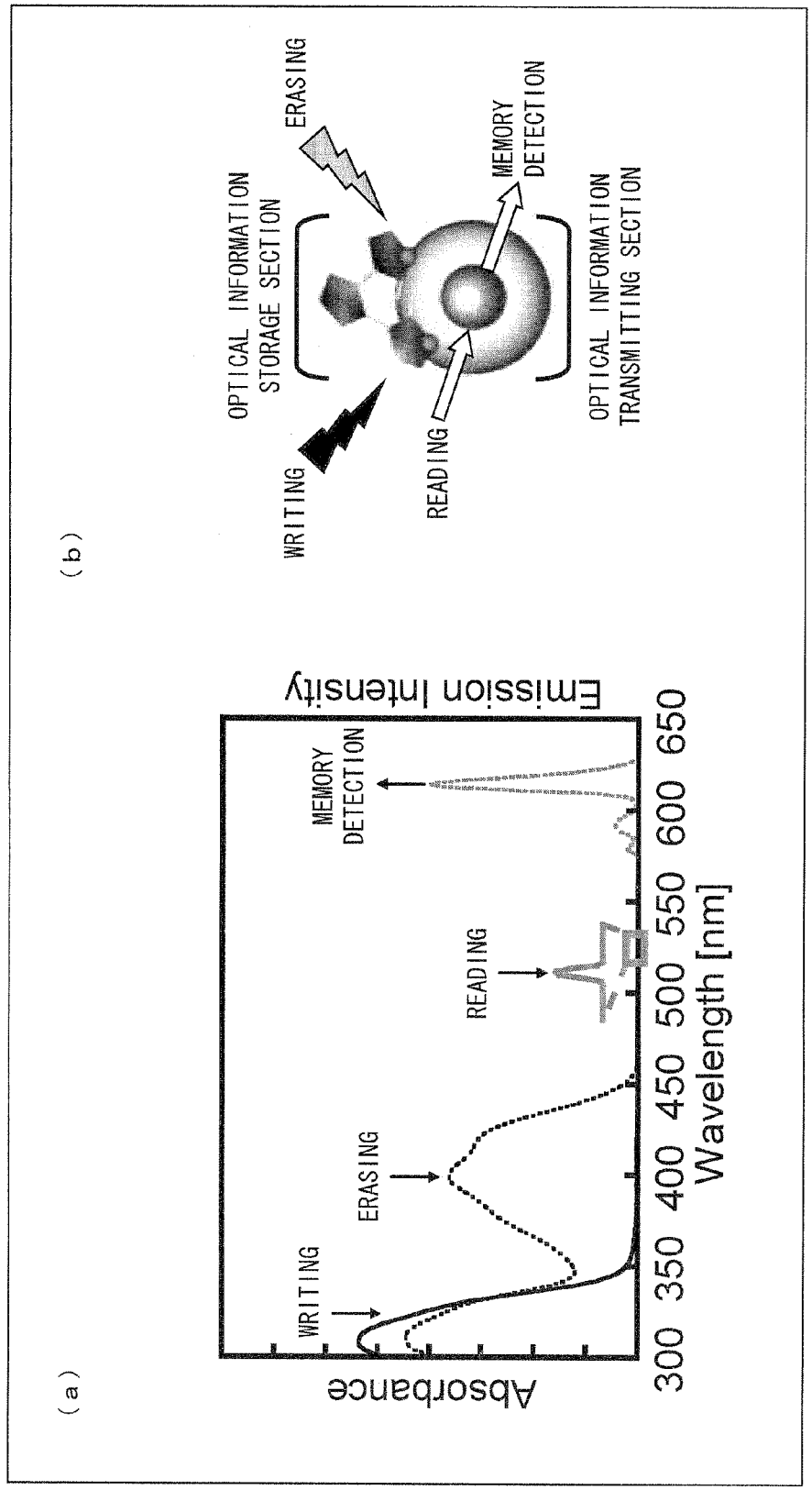
FIG. 5 schematically illustrates a property of a metal complex of the present invention, where (a) is a graph schematically illustrating transition of diarylethene and a metal ion and (b) is a diagram schematically illustrating a function of diarylethene and the metal ion.
Figure 6:
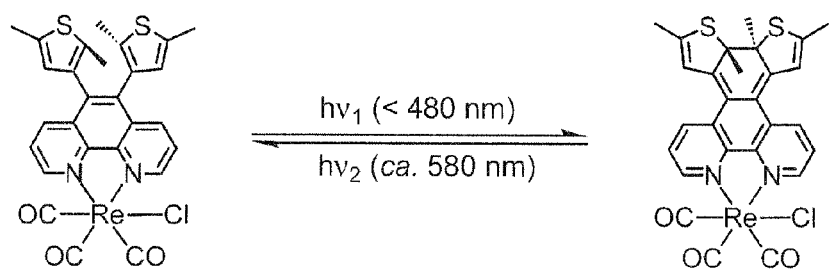
FIG. 6 is a diagram illustrating a conventional technique, the diagram illustrating a photochromic reaction in a metal complex in which is coordinated a ligand incorporating diarylethene in phenanthroline.
Figure 7:
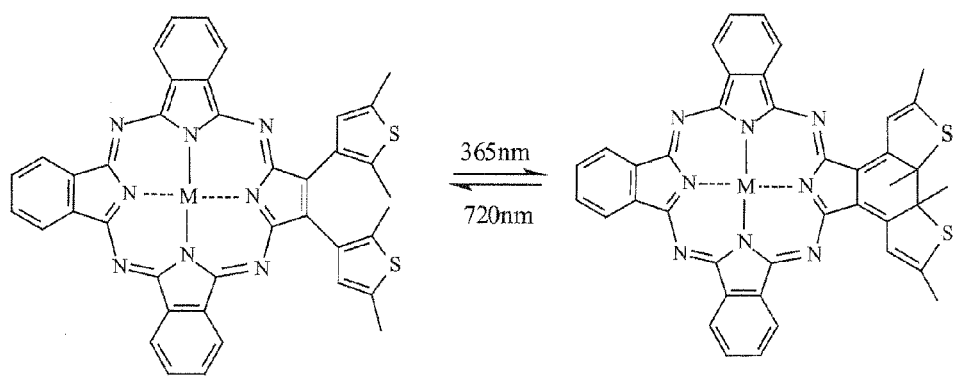
FIG. 7 is a diagram illustrating a conventional technique, the diagram illustrating a photochromic reaction in a complex in which a photochromic site has been introduced in phthalocyanine.

The metal complex of the present invention, in contrast, has absorption bands (for write and erase) for the photochromic molecule, the absorption bands being different from an absorption band for the metal complex, that wavelengths of exciting light (for readout) and emission wavelengths for the metal complex (for memory detection) (see, for example, (a) of FIG. 5). The metal complex of the present invention thus makes it possible to read out optically stored information without destructing it.

The metal complex of the present invention thus makes it possible to use a light beam with the wavelength $\lambda 1$ to, for example, input information or a signal to the photochromic molecule or write (or store) information or a signal to the photochromic molecule. The metal complex of the present invention further makes it possible to use a light beam with the wavelength $\lambda 3$ to, for example, output the above information or signal, inputted or stored in the photochromic molecule, or read out (or reproduce) the information or signal. The metal complex of the present invention still further makes it possible to use a light beam with the wavelength $\lambda 2$ to, for example, erase the information or signal inputted or stored in the photochromic molecule. Since (i) the wavelengths $\lambda 1$, $\lambda 2$, and $\lambda 3$ are different from one another, and (ii) the absorption bands for the photochromic molecule are different from $\lambda 3$ and emission wavelengths of the metal complex, there is no interference between (i) input and storage of information or a signal, output and reproduction thereof, and (ii) erasing thereof. The metal complex of the present invention is thus usable as, for example, an information storage medium, a non-volatile memory, and a switching element.

Stated differently, the metal complex of the present invention includes (i) a photochromic molecule serving as an optical information storage section, and (ii) a metal ion serving as an optical information transmitting section, which are independent of each other, as schematically illustrated in (b) of FIG. 5.

In the metal complex of the present invention, the photochromic molecule and the metal ion respond to light independently of each other: Irradiating the metal complex of the present invention with a light beam having the wavelength $\lambda 1$ causes the photochromic molecule, serving as the optical information storage section, to undergo a photochromic reaction, by which the photochromic molecule changes its molecular structure from an opened-ring form to a closed-ring form. Then irradiating the metal complex with a light beam having the wavelength $\lambda 2$ causes the photochromic molecule having a molecular structure changed as above, that is, the photochromic molecule having a closed-ring form, to return to its original molecular structure, that is, an opened-ring form. The wavelengths $\lambda 1$ and $\lambda 2$ are different from each other and particular for the photochromic molecule. The optical information storage section in the metal complex of the present invention can thus reversibly change its molecular structure between an opened-ring form and a closed-ring form with use of light beams having the respective wavelengths $\lambda 1$ and $\lambda 2$.

The optical information storage section in the metal complex of the present invention, that is, the photochromic molecule, does not respond to a light beam having the wavelength $\lambda 3$. Specifically, since the wavelength $\lambda 3$ for detecting light emitted by the metal complex is different from an absorption wavelength of the photochromic molecule, a light beam having the wavelength $\lambda 3$ does not induce a change in the molecular structure of the photochromic molecule. On the other hand, the optical information transmitting section in the metal complex, that is, the metal ion, does not respond to a light beam of either the wavelength $\lambda 1$ or the wavelength $\lambda 2$. Specifically, the metal ion is not excited by a light beam of either the wavelength $\lambda 1$ or the wavelength $\lambda 2$ for light emission.

The wavelength $\lambda 3$ is different from either the wavelength $\lambda 21$ or the wavelength $\lambda 2$. This ensures that the photochromic molecule and the metal ion in the metal complex of the present invention respond to light independently of each other.

The following describes a principle of "optical write." The photochromic molecule changes its structure due to "write light" (having the wavelength $\lambda 1$). This means that the metal ion, to which the photochromic molecule is coordinated, changes its ligand field. Such a change in the ligand field changes the light emission property of the metal ion. Thus, detecting such a change in the light emission property with use of a light beam having a wavelength different from the absorption wavelength of the photochromic molecule makes it possible to read out optical information.

In the present invention, respective light beams of the wavelengths $\lambda 1$, $\lambda 2$, and $\lambda 3$ are each not limited to a light beam having a single wavelength, and may each be a light beam having a particular wavelength range.

The wavelengths $\lambda 1$, $\lambda 2$, and $\lambda 3$ each have a value that changes in correspondence with the metal ion and the photochromic molecule in use. Respective values of the wavelengths $\lambda 1$, $\lambda 2$, and $\lambda 3$ fall within ranges of, for example, 200 to 600 nm, 350 to 800 nm, and 450 to 1000 nm, respectively. The wavelengths $\lambda 1$, $\lambda 2$, and $\lambda 3$ are, however, not limited to these. Further, while irradiating the metal complex with light beams of the respective wavelengths $\lambda 1$ and $\lambda 2$ to reversibly change the molecular structure of the photochromic molecule results in the photochromic molecule having respective molecular structures both different from the original molecular structure, the metal complex including such a photochromic molecule having a different molecular structure is not particularly limited in terms of its absorption band wavelengths. The metal complex including the photochromic molecule having either of the molecular structures different from the original molecular structure preferably has absorption band wavelengths that are shorter than the wavelength $\lambda 3$.

<Capabilities of the Metal Complex of the Present Invention>

The metal complex of the present invention exhibits capabilities described below.

First, the metal complex of the present invention, through a photochromic reaction induced by a light beam having either the wavelength $\lambda 1$ or the wavelength $\lambda 2$, reversibly changes its structure between two states. There is no particular limit to how to irradiate such a light beam for inducing a photochromic reaction in the metal complex of the present invention. A light beam with either the wavelength $\lambda 1$ or the wavelength $\lambda 2$ may thus be irradiated with use of any device. The structure of the photochromic molecule can be changed by irradiation of a light beam of a desired wavelength with use of a typical light source such as an LED, a heavy hydrogen lamp, a xenon lamp, a halogen lamp, and a laser.

Second, the metal complex of the present invention emits light when excited by a light beam having the wavelength 3, and has a light emission property for light that it emits when excited by a light beam having the wavelength $\lambda 3$, the light emission property being different between (i) after the metal complex has been irradiated with a light beam having the wavelength $\lambda 1$ and (ii) after the metal complex has been irradiated with a light beam having the wavelength $\lambda 2$. There is no particular limit to how to irradiate the metal complex of the present invention with a light beam for exciting the metal complex. The metal complex can be irradiated with a light beam of the wavelength $\lambda 3$ with use of any device. The metal ion can be caused to emit light by irradiation of desired exciting light with use of a typical exciting light source such as an LED, a heavy hydrogen lamp, a xenon lamp, and a halogen lamp.

Third, in the metal complex of the present invention, a light beam with the wavelength $\lambda 3$ for detecting light emitted by the metal complex does not induce a change in the molecular structure of the photochromic molecule. This prevents the light emission property, such as the emission intensity, from being changed by continuous irradiation of a light beam having the wavelength $\lambda 3$, and consequently makes it possible to read out written information without destructing it.

Fourth, the metal complex of the present invention can change its light emission property, such as the emission intensity, depending on the intensity or duration of irradiation of a light beam having the wavelength $\lambda 1$ for write.

(II) Composition of the Present Invention

A composition of the present invention contains the above-described metal complex of the present invention and a medium. The composition may contain either a single kind of the above-described metal complex of the present invention or a mixture of a plurality of kinds of the metal complex. There is no particular limit to an amount of the metal complex of the present invention contained in the composition of the present invention. The amount is set as appropriate in correspondence with an application or a kind of the above medium.

The composition of the present invention, which contains the metal complex of the present invention as mentioned above, exhibits unique responses to three different light beams having the respective wavelengths $\lambda 1$, $\lambda 2$, and $\lambda 3$). Specifically, the composition of the present invention emits light upon irradiation of a light beam having the wavelength $\lambda 3$. This is because the metal ion in the metal complex contained in the composition is excited by such irradiation of a light beam with the wavelength $\lambda 3$ to emit light. Further, the composition of the present invention has a light emission property for light that it emits upon irradiation of a light beam having the wavelength $\lambda 3$, which light emission property can be changed reversibly with use of a light beam having the wavelength $\lambda 1$ or a light beam having the wavelength $\lambda 2$. This is because the photochromic molecule in the metal complex contained in the composition reversibly changes its molecular structure through a photochromic reaction induced by a light beam having the wavelength $\lambda 1$ or a light beam having the wavelength $\lambda 2$.

The composition of the present invention can thus change its light emission property, that is, its emission intensity, with use of a light beam having the wavelength $\lambda 1$ or a light beam having the wavelength $\lambda 2$. This indicates that the composition of the present invention can amplify and attenuate light at a high speed with use of light. The composition of the present invention is thus usable as a switching element such as a high-speed switch. Such a switching element is usable in, for example, a control system for an optical amplification device. In other words, the switching element is usable in optical information communications.

The metal complex of the present invention has absorption bands (for write and erase) for the photochromic molecule, the absorption bands being different from an absorption band for the metal complex, that is, wavelengths of exciting light (for readout) and emission wavelengths for the metal complex (for memory detection). The metal complex of the present invention thus makes it possible to read out optically stored information without destructing it.

As with the metal complex of the present invention, the composition of the present invention is thus highly suitably usable in an information storage medium for recording or storing, for example, information or a signal. Further, with use of (i) the light emission property of the composition of the present invention and (ii) the property by which the composition of the present invention changes its light emission property through a photochromic reaction, the composition of the present invention is usable in an information identifying medium such as an ID card. Specifically, the metal complex of the present invention has a light emission property and a photochromic reactivity both varying according to respective kinds of the photochromic molecule and the metal ion included in the metal complex. The metal complex of the present invention can thus function as a code, which can be deciphered on the basis of (i) the light emission property of the metal complex and (ii) a change caused in the light emission property by a photochromic reaction. The composition containing the metal complex of the present invention as a code is thus usable in an information identifying medium.

The medium contained in the composition of the present invention is not particularly limited. A preferable medium may simply be selected as appropriate in correspondence with an application of the composition.

Specific examples of the medium include an organic solvent, a resin, an inorganic material, and an organic-inorganic hybrid material.

Examples of the organic solvent include: an aromatic hydrocarbon solvent such as benzene, toluene, xylene, ethylbenzene, trimethylbenzene, diethylbenzene, and isopropylbenzene; an aliphatic hydrocarbon solvent such as an alkane and a cycloalkane; a halogenated hydrocarbon solvent such as dichloromethane, 1,2-dichloroethane, tetrachloroethane, trichloroethylene, methyl iodide, chloroform, carbon tetrachloride, chlorobenzene, and dichloronaphthalene; a ketone solvent such as acetone, methyl ethyl ketone, methyl isobutyl ketone, diethyl ketone, diisobutyl ketone, cyclopentanone, and cyclohexanone; an ether solvent such as diethyl ether, dimethoxy ethane, diethoxy ethane, tetrahydrofuran, and tetrahydropyran; an ester solvent such as methyl acetate, ethyl acetate, butyl acetate, acetic acid isoamyl, ethyl formate, butyl formate, Cellosolve acetate and Carbitol acerate; and an alcohol solvent such as methanol, ethanol, isopropyl alcohol, butanol, Cellosolve, ethyl Cellosolve, butyl Cellosolve, Carbitol, ethyl Carbitol, butyl Carbitol, and diacetone alcohol. Either a single one of the above organic solvents may be used individually, or a plurality of the organic solvents may be used in combination.

Examples of the above resin include a polyimide resin, a polyamide resin, a polymethyl methacryl resin, a polyacrylate, a polystyrene resin, a polyethylene naphthalate resin, a polyester resin, a polyurethane, a polycarbonate resin, an epoxy resin, a polyethylene terephthalate resin, a vinyl chloride resin, a vinylidene chloride resin, an acrylonitrile-butadiene-styrene (ABS) resin, an acrylonitrile styrene (AS) resin, a cycloolefin resin, a siloxane polymer, and a halide or deuteride thereof. Either a single one of the above resins may be used individually, or a mixture of two or more of the resins may be used.

Examples of the above inorganic material include, for example, a glass produced by sol-gel method.

The composition of the present invention, which can include any of the above example mediums, preferably includes a medium that is high in compatibility with the metal complex of the present invention.

The composition of the present invention may further contain, in correspondence with its application or the like, an additive for providing a particular function. Examples of the additive include an antioxidant, an inorganic filler, a stabilizer, an antistatic agent, a dye, a pigment, a flame retardant, an inorganic filler, and an elastomer for improving impact resistance. The composition of the present invention may also contain an additive, such as a lubricant, that improves workability of the composition of the present invention. The composition of the present invention, in the case where it is cast-flown to form a cast film, may include a leveling agent.

Examples of the above antioxidant include 2,6-di-t-butyl-4-methyl phenol, 2,2'-dioxy-3,3'-di-t-butyl-5,5'-dimethyl phenyl methane, tetrakis[methylene-3-(3,5-di-t-butyl-4-hydroxyphenyl)propionate]methane, 1,1,3-tris(2-methyl-4-hydroxy-5-t-butyl phenyl)butane, 1,3,5-trimethyl-2,4,6-tris(3,5-di-t-butyl-4-hydroxy benzyl-benzene, stearyl-$\beta$-(3,5-di-t-butyl-4-hydroxyphenyl)propionate, 2,2'-dioxy-3,3'-di-t-butyl-5,5'-diethyl phenyl methane, 3,9-bis[1,1-dimethyl-2-[$\beta$-(3-t-butyl-4-hydroxy-5-methyl phenyl)propionyl oxy]ethyl], 2,4,8,10-tetraoxaspiro[5,5]undecane, tris(2,4-di-t-butyl phenyl)phosphite, cyclic neopentane tetrayl bis(2,4-di-t-butyl phenyl)phosphite, cyclic neopentane tetraylbis(2,6-di-t-butyl-4-methyl phenyl)phosphite, and 2,2-methylene bis (4,6-di-t-butyl phenyl)octyl phosphite.

Examples of the above inorganic filler include calcium carbonate, carbon fiber, and a metal oxide.

Examples of the above leveling agent include a fluorine nonionic surface active agent, a special acrylic resin leveling agent, and a silicone leveling agent.

The composition of the present invention is not particularly limited in form, and may thus have any form. Examples of the form include a film, a plate, powder, grains, granules, paste, liquid, and emulsion.

How to produce the composition of the present invention is not particularly limited. A suitable method may simply be selected as appropriate in correspondence with, for example, how the composition is composed, its form, and/or its application. In the case of producing the composition in the form of powder, for example, the composition can be produced by a method in which the metal complex of the present invention, the medium, and according to need, other additives listed above as examples are mixed in a biaxial extruder, a brabender, or a roll kneader, and the resulting mixture is then formed into a pellet in an extruder. The pellet may further be ground in a grinder into powder.

In the case of producing the composition in the form of liquid, the composition can be produced by, for example, a method in which the metal complex of the present invention, the medium, and according to need, other additives listed above as examples are dissolved or dispersed in a suitable solvent.

The following describes use of the composition of the present invention. The composition of the present invention is suitably usable in production of, for example: a high-speed switching element usable in an optical amplification method described below; a memory device, an information storage medium, and an optical memory each suitably usable in an information recording and reproduction method described below; and an information identifying medium, such as an ID card, that is suitably usable in an information identifying method described below.

The description below deals with, as an embodiment of the use of the composition of the present invention, an information storage medium including the composition.

A specific example of such an information storage medium is an information storage medium in which a recording layer is formed on each or either side of a substrate.

The information storage medium of the present invention, for example, simply includes the composition of the present invention in the recording layer. The recording layer has a thickness that falls preferably within a range from 0.01 μm to 3.0 mm, or more preferably within a range from 0.05 μm to 1.0 mm. If the thickness of the recording layer is less than 0.01 μm, the recording layer may not exhibit its recording and displaying capabilities sufficiently. If the thickness of the recording layer exceeds 3.0 mm, on the other hand, it may be difficult to form a recording layer that is flat over the entire surface.

The substrate is made of, for example, a thermoplastic resin, glass, or paper. Examples of the thermoplastic resin include a polymethyl methacryl resin, a polystyrene resin, a polyethylene terephthalate resin, a polyethylene naphthalate resin, a polycarbonate resin, a polyamide resin, a vinyl chloride resin, a vinylidene chloride resin, an acrylonitrile-butadiene-styrene (ABS) resin, an acrylonitrile styrene (AS) resin, and a cycloolefin resin.

How to produce the information storage medium is not particularly limited. The information storage medium can be produced by, for example, a method in which (i) a solution of the composition of the present invention is cast-flown over the substrate, and (ii) a solvent of the solution is removed from the resulting solution layer so that a recording layer is formed on the substrate. How to cast-flow the composition over the substrate is not particularly limited. The composition can be cast-flown by a method that has been publicly known, for example, with use of a bar coater.

The information storage medium can also be produced by forming a film of the composition of the present invention on a surface of the substrate. How to form a film of the composition of the present invention on the surface of the substrate is not particularly limited. Such a film can be formed by a method that has been publicly known. Examples of the method include (i) a wet process such as brush coating, dip coating, spray coating, plate coating, spinner coating, bead coating, and curtain coating, and (ii) a film forming method such as photogravure, screen printing, offset printing, and letterpress.

The information storage medium can further be produced by (i) molding the composition of the present invention so that the substrate is formed integrally with a recording layer or (ii) placing a film of the composition of the present invention on the substrate. Specifically, the information storage medium can be produced by, for example, molding a composition prepared by mixing the metal complex of the present invention with a resin mentioned above as an example of the medium. The information storage medium may be provided with, for example, a surface protection film on the recording layer.

The composition of the present invention can alternatively be used in the form of liquid. The information storage medium can be produced by, for example, a method in which (i) the metal complex of the present invention is dissolved in a suitable solvent (for example, a solvent mentioned above as an example usable in production) and (ii) the composition of the present invention in the form of a solution is contained in, for example, a glass cell.

The above high-speed switching element and information identifying medium can each also be produced by a suitable method selected as appropriate.

(III) Light Intensity Adjustment Method

The metal complex of the present invention is capable of amplifying light at a high speed with use of light. The present invention thus further encompasses a light intensity adjustment method involving use of the metal complex of the present invention. The present invention still further encompasses (i) an optical switch based on the light intensity adjustment method and (ii) an optical amplification device including the optical switch.

The optical switch of the present invention is simply required to include the metal complex of the present invention. There is no particular limit to other aspects such as an arrangement and a shape. The optical switch can be produced by including the composition of the present invention. The following describes the light intensity adjustment method of the present invention in detail.

The light intensity adjustment method of the present invention is simply such a method as follows: When a metal complex that has a structure in which a photochromic molecule coordinates to a metal ion is excited by a light beam having the wavelength $\lambda 3$, an intensity of light emitted by the metal complex is controlled with use of a light beam having the wavelength $\lambda 1$ and a light beam having the wavelength $\lambda 2$. There is no particular limit to other details of the arrangement.

In other words, the light intensity adjustment method is a method for amplifying and attenuating light with use of light on the basis of a property of the above-described metal complex of the present invention.

The light intensity adjustment method of the present invention, which amplifies and attenuates light with use of light, is capable of amplifying and attenuating light at an extremely high speed. The light intensity adjustment method of the present invention is thus applicable to a control system for an optical amplification device. This indicates that the light intensity adjustment method is also applicable in high-speed switching for optical information communications.

(IV) Information Recording and Reproduction Method

The metal complex of the present invention, as described above, suitably finds an application in recording and reproduction of information. The present invention thus encompasses an information recording and reproduction method based on the metal complex of the present invention. The present invention further encompasses (i) an information storage medium and molecule memory both for use in the information recording and reproduction method and (ii) an information recording and reproduction device for implementing the method.

The information storage medium and molecule memory of the present invention can be produced by, as described above, processing the composition of the present invention. The following describes the information recording and reproduction method of the present invention in detail.

The information recording and reproduction method of the present invention is simply required to include (A) a step (hereinafter referred to also as "recording step") for, by emitting a light beam with the wavelength $\lambda 1$ onto a metal complex having a structure in which a photochromic molecule coordinates to a metal ion, recording information in the photochromic molecule and (B) a step (hereinafter referred to also as "reproduction step") for, by (i) irradiating the metal complex with a light beam having the wavelength $\lambda 3$, (ii) receiving light thus emitted by the metal complex, and (iii) measuring an emission intensity of the light emitted, reproducing the information, stored in the photochromic molecule, on the basis of the measured emission intensity of the light emitted. There is no particular limit to other details of the arrangement. The reproduction step may be varied to measure a value other than an emission intensity of the metal complex, such as a light emission quantum yield light emission duration of the metal complex and the like, to (i) reproduce the stored information on the basis of the measured value such as the light emission quantum yield, the light emission duration and the like or to (ii) reproduce the stored information on the basis of a radiation rate constant calculated from the light emission quantum yield and the light emission duration. The information recording and reproduction method of the present invention may further include, in addition to the recording step and the reproduction step, a step (hereinafter referred to also as "erasing step") for erasing the information, stored in the photochromic molecule, by irradiating the metal complex with a light beam having the wavelength $\lambda 2$. The following describes the recording step, the reproduction step, and the erasing step in detail.

(IV-1) Recording Step

The recording step involves irradiating the metal complex of the present invention with a light beam of the wavelength $\lambda 1$ to cause the photochromic molecule in the metal complex to change its form from an opened-ring form to a closed-ring form. Utilizing such a structural change allows information to be recorded in the photochromic molecule. In the case of recording information in the information storage medium of the present invention, irradiating the information storage medium with a light beam having the wavelength $\lambda 1$ and focused on the recording layer causes photochromic molecules that are included in the metal complex of the present invention and that are present at an irradiated portion of the information storage medium to each change its structure to record information.

The wavelength $\lambda 1$ is not particularly limited, and is determined in correspondence with the kind of the photochromic molecule. The wavelength $\lambda 1$ preferably falls within an ultraviolet range. Further, there is no particular limit to how to irradiate the metal complex with a light beam of the wavelength $\lambda 1$ during the recording step. The metal complex can be irradiated with such a light beam by a method that uses, for example, a heavy hydrogen lamp, a xenon lamp, a mercury lamp, a halogen lamp, an LED, or a laser.

In addition, there is also no particular limit to how long the metal complex is irradiated with a light beam of the wavelength $\lambda 1$ during the recording step. The metal complex is irradiated with such a light beam for one picosecond or longer, for example.

(IV-2) Reproduction Step

The reproduction step involves (i) irradiating the metal complex of the present invention with a light beam of the wavelength $\lambda 3$ to cause the metal complex to emit light, and (ii) measuring an emission intensity of the emitted light to reproduce, on the basis of the emission intensity, information stored in the photochromic molecule during the recording step. More specifically, the reproduction step involves first emitting a light beam having the wavelength $\lambda 3$ onto the metal complex in which information was stored during the recording step. This operation excites the metal complex to emit light. The reproduction step involves next (i) measuring an emission intensity of the light thus emitted, and (ii) determining, on the basis of the measured emission intensity, whether the photochromic molecule included in the metal complex has an opened-ring form or a closed-ring form. This operation allows the information stored in the metal complex to be reproduced.

In the case of reproducing information stored in the information storage medium of the present invention, the reproduction step involves (i) irradiating the information storage medium with a light beam having the wavelength $\lambda 3$ and focused on the recording layer, and thus (ii) measuring an emission intensity of light emitted by metal complex molecules present at an irradiated portion of the information storage medium. The reproduction step involves next determining, on the basis of the measured emission intensity of the light emitted by each metal complex, whether the photochromic molecule included in each metal complex has an opened-ring form or a closed-ring form. This operation allows the information stored in the information storage medium to be reproduced.

The wavelength λ3 is not particularly limited, and is determined in correspondence with the kind of the metal ion. Further, there is no particular limit to how to irradiate the metal complex with a light beam of the wavelength λ3 during the reproduction step. The metal complex can be irradiated with such a light beam by a method that uses, for example, a heavy hydrogen lamp, a xenon lamp, a mercury lamp, a halogen lamp, an LED, or a laser.

In addition, there is also no particular limit to how long the metal complex is irradiated with a light beam of the wavelength λ3 during the recording step. The metal complex is irradiated with such a light beam for one picosecond or longer, for example.

The expressions as used herein about measuring the emission intensity of emitted light refer to all of (i) measuring the intensity of the entire light that is not dispersed into spectra, (ii) measuring the respective intensities of dispersed emission spectra, and (iii) measuring only the intensity of a line spectrum having a particular wavelength, the line spectrum being among dispersed emission spectra. In other words, the reproduction step may involve (i) measuring the intensity of the entire light, emitted by the metal complex, without dispersing it into spectra, (ii) measuring the respective intensities of dispersed emission spectra of the emitted light, or (iii) measuring only the intensity of a line spectrum having a particular wavelength, the line spectrum being among dispersed emission spectra of the emitted light.

In the case where the reproduction step involves measuring the intensity of the entire light, it is possible to (i) simplify an arrangement of a device for measuring the emission intensity and (ii) reduce a period necessary for the reproduction step. In the case where the reproduction step involves measuring the respective intensities of dispersed emission spectra of the emitted light, it is possible to improve accuracy in identifying information. In the case where the reproduction step involves measuring only the intensity of a line spectrum having a particular wavelength, the line spectrum being among dispersed emission spectra of the emitted light, it is possible to (i) simplify an arrangement of a device for measuring the emission intensity, (ii) reduce a period necessary for the reproduction step, and (iii) improve accuracy in identifying information.

The reproduction step in the information recording and reproduction method of the present invention preferably involves measuring only the intensity of a line spectrum having a particular wavelength, the line spectrum being among dispersed emission spectra of the light emitted by the metal complex or the information storage medium. In this case, there is no particular limit to the number of wavelengths to be selected. The number may be one (1), or may be two or more. Increasing the number of wavelengths to be selected can improve accuracy in reproducing information. Selecting two wavelengths, for example, makes it possible to determine, on the basis of a ratio of respective intensities of line spectra of the two wavelengths, whether the photochromic molecule in the metal complex has an opened-ring form or a closed-ring form. Selecting two wavelengths as such thus allows information to be reproduced with greater accuracy. Further, selecting two wavelengths reduces a time necessary for the reproduction step, and thus allows information to be read out at higher speed.

There is no particular limit to the above wavelengths to be selected. The wavelengths may simply be selected as appropriate in correspondence with a light emission property of the kind of the metal complex or the information identifying medium in use. The wavelengths to be selected may be, for example, a wavelength of a light beam caused by magnetic dipole transition or electric dipole transition. The present invention particularly preferably selects both of the wavelengths of respective light beams caused by magnetic dipole transition and electric dipole transition. The wavelengths of the respective light beams caused by magnetic dipole transition and electric dipole transition depend on the kind of the metal complex.

The present invention can determine the structure of the photochromic molecule by, for example, comparing (i) the emission intensity measured during the reproduction step with (ii) an emission intensity associated with the opened-ring form and an emission intensity associated with the closed-ring form.

The expressions as used herein about comparing emission intensities refer, in the case where the reproduction step involves measuring the intensity of the entire light emitted by the metal complex, to comparing the emission intensity of the entire light with an emission intensity associated with the opened-ring form and an emission intensity associated with the closed-ring form.

Further, the expressions refer, in the case where the reproduction step involves measuring the respective intensities of dispersed emission spectra of the emitted light, to (i) comparing the respective intensities of emission spectra with an intensity of an emission spectrum associated with the opened-ring form and an intensity of an emission spectrum associated with the closed-ring form and to (ii) calculating a ratio of the respective intensities of line spectra having particular wavelengths, the line spectra being among the emission spectra targeted for measurement during the reproduction step, and thus comparing the ratio with a ratio associated with the opened-ring form and a ratio associated with the closed-ring form. The latter measurement makes it possible to increase a reproduction speed and improve reproduction accuracy.

In the case where the reproduction step involves measuring only the intensity of a line spectrum having a particular wavelength, the line spectrum being among dispersed emission spectra of the emitted light, the expressions about comparing emission intensities refer to comparing respective intensities of a plurality of line spectra, the intensities having been measured during the reproduction step, with an intensity of a line spectrum associated with the opened-ring form and an intensity of a line spectrum associated with the closed-ring form. Further, in the case where the reproduction step involves measuring respective intensities of a plurality of line spectra having particular wavelengths, the expressions refer, in addition to the above comparison, to calculating a ratio of respective intensities of a plurality of line spectra, the intensities having been measured during the reproduction step, and thus comparing the ratio with a ratio associated with the opened-ring form and a ratio associated with the closed-ring form. In the latter case, it is possible to increase a reproduction speed and improve reproduction accuracy.

In the case of calculating a ratio of respective intensities of line spectra, the present invention may calculate a ratio of either respective intensities of two line spectra or respective intensities of three or more line spectra. Calculating a ratio of respective intensities of more line spectra can improve reproduction accuracy.

The reproduction step may involve reproducing the information, stored in the photochromic molecule, on the basis of a light emission quantum yield, a light emission duration, a radiation rate constant calculated from the light emission quantum yield and the light emission duration, or a combination of two or more of these values. In other words, the reproduction step may involve (i) irradiating the metal complex of the present invention with a light beam of the wavelength λ3 to cause the metal complex to emit light, (ii) measuring at least one of a light emission quantum yield and light emission duration of the light emitted, and (iii) reproducing the information, stored in the photochromic molecule, on the basis of at least one of the light emission quantum yield, the light emission duration, and the radiation rate constant. A more specific reproduction method is similar to that for the case of reproducing information on the basis of an emission intensity. There is no particular limit to how to measure a light emission quantum yield and a light emission duration. The light emission quantum yield may be measured by either an absolute method or a relative method.

The radiation rate constant is calculated from the light emission quantum yield and the light emission duration by Formulae (1) and (2) below.

$$\Phi_{emi} = \frac{k_r}{k_r + k_{nr}} \quad (1)$$

$$\tau_{emi} = \frac{1}{k_r + k_{nr}} \quad (2)$$

In Formulae (1) and (2), $\Phi_{emi}$ is a light emission quantum yield; $\tau_{emi}$ is a light emission duration; $k_r$ is a radiation rate constant; and $k_{nr}$ is a nonradiative rate constant.

The reproduction step may involve reproducing the information, stored in the photochromic molecule, on the basis of the above emission intensity, a combination of a plurality of emission intensities, a light emission quantum yield, a light emission duration, a radiation rate constant calculated from the light emission quantum yield and the light emission duration, or a combination of two or more of these values. This operation can improve reproduction accuracy further.

The information recording and reproduction method of the present invention, which uses the metal complex or information storage medium of the present invention, does not allow information to be erased from the metal complex or information storage medium unless the metal complex is irradiated with a light beam of the wavelength λ2 so that the photochromic molecule changes its form from the closed-ring form to the opened-ring form. This arrangement consequently allows information stored in the metal complex or information storage medium to be reproduced any number of times.

(IV-3) Erase Step

The erasing step involves irradiating the metal complex of the present invention with a light beam of the wavelength λ2 so that the photochromic molecule in the metal complex changes its form from the closed-ring form to the opened-ring form. Changing the form of the photochromic molecule as such erases information stored in the photochromic molecule. In the case of erasing information stored in the information storage medium of the present invention, irradiating the entire recording layer with a light beam having the wavelength λ2 erases the information stored.

The wavelength λ2 is not particularly limited, and is determined in correspondence with the kind of the photochromic molecule. The wavelength λ2 preferably falls within a visible range.

There is no particular limit to how to irradiate the metal complex with a light beam of the wavelength λ2 during the erasing step. The metal complex can be irradiated with such a light beam by a method that uses, for example, a heavy hydrogen lamp, a xenon lamp, a mercury lamp, a halogen lamp, an LED, or a laser.

In addition, there is also no particular limit to how long the metal complex is irradiated with a light beam of the wavelength λ2 during the erasing step. The metal complex is irradiated with such a light beam for one picosecond or longer, for example.

The metal complex and information storage medium, from which information stored therein has been erased as above, can be used to record information again through the recording step. The metal complex and information storage medium of the present invention can repeat information recording and information erasing.

As described above, the information recording and reproduction method of the present invention uses the metal complex of the present invention and respective light beams of the wavelengths λ1, λ2, and λ3 to record, reproduce, and erase information in a repeated manner. The wavelengths λ1, λ2, and λ3 are different from one another.

The present invention encompasses an information recording and reproduction device including constituent members for carrying out the above respective steps of the information recording and reproduction method of the present invention. The information recording and reproduction device of the present invention is simply required to include constituent members that are capable of carrying out the above respective steps. There is thus no particular limit to details of the arrangement. The information recording and reproduction device of the present invention can include, for example: a light source section for carrying out the recording step; a light source section, a light receiving section, an emission intensity measuring section and an emission intensity calculating section each for carrying out the reproduction step; and a light source section for carrying out the erasing step.

(V) Information Identifying Method

The metal complex of the present invention, as described above, has the function as a code. The present invention thus encompasses an information identifying method that uses the metal complex of the present invention. The present invention further encompasses an information identifying medium for use in the information identifying method and an information identifying device for implementing the method.

The composition containing the metal complex of the present invention, as described above, can be included in the information identifying medium. In other words, the information identifying medium of the present invention includes the composition described in (II) above.

The information identifying medium is not particularly limited in shape or form. Specific examples of the shape and form of the information identifying medium of the present invention include a card, a film, a sticker, and an armband each produced by molding a resin containing the metal complex of the present invention. The information identifying medium may also be an image, a figure, or a character each printed with use of an ink containing the metal complex of the present invention.

The above ink includes the composition described in (II) above, and can be produced by dispersing the metal complex of the present invention in a medium and, according to need, adding an additive. The medium used as above is not particularly limited as long as it is a medium typically used for ink. Suitable examples of the medium include those mentioned in (II) above.

The above ink is usable as the information identifying medium, particularly as a code medium, as follows, for example: First, the ink is applied or printed on each or either side of a substrate such as a label, a card, a film, and a sticker. The ink thus applied or printed is not particularly limited in color. In the case where the ink is, for example, transparent, white, or faintly colored, the ink, which is invisible as applied or printed, can provide improved security. There is also no particular limit to how to apply or print the ink. Suitable examples of the method include a method described in (II) above for use in the production of the information storage medium. Another suitable method is inkjet printing.

Then, the applied or printed ink is irradiated with a light beam having the wavelength $\lambda 1$. This causes the photochromic molecule in the metal complex to change its form from an opened-ring form to a closed-ring form. Utilizing such a structural change allows code information to be written (or recorded) in the photochromic molecule. Alternatively, the ink can be irradiated with a light beam having the wavelength $\lambda 2$. This causes the photochromic molecule in the metal complex to change its form from the closed-ring form to the opened-ring form and thus to erase code information stored in the photochromic molecule.

Next, the ink, in which information has been recorded as above or from which information has been erased as above, is irradiated with a light beam (exciting light) having the wavelength $\lambda 3$. Since this operation causes the metal complex included in the ink to emit light, measuring an emission intensity, a light emission quantum yield, a light emission duration and/or the like makes it possible to read information that has been recorded or erased. Alternatively, information recorded or erased can be read on the basis of an emission intensity, a combination of a plurality of emission intensities, a light emission quantum yield, a light emission duration, a radiation rate constant calculated from the light emission quantum yield and the light emission duration, or a combination of two or more of these values. This operation can improve read accuracy.

The information identifying medium of the present invention uses readout light (that is, a light beam having the wavelength $\lambda 3$), write light, and erase light which are different from one another in wavelength. The information identifying medium is thus advantageous in that readout of information does not degrade code information, that is, information recorded or erased. Further, selecting a rare-earth ion as the metal included in the metal complex allows an emission wavelength to change from the visible range to the near-infrared range. In addition, combining a metal ion with a photochromic molecule makes it possible to freely change readout light, write light, and erase light, and consequently provides a more secure code.

The information identifying medium of the present invention may include either a single kind of the metal complex or a plurality of kinds of the metal complex. The information identifying medium, however, preferably includes a plurality of kinds of metal complex for an improved identification ability (that is, improved security).

The above information identifying medium of the present invention can be produced by, as described above, processing the composition of the present invention.

The following describes the information identifying method of the present invention in detail. The information identifying method of the present invention is simply required to include (i) a step (hereinafter referred to also as "first irradiation step") for irradiating, with a light beam having the wavelength $\lambda 1$, a metal complex having a structure in which a photochromic molecule coordinates to a metal ion, (ii) a step (hereinafter referred to also as "first light emission measuring step") for irradiating the metal complex after the first irradiation step with a light beam having the wavelength $\lambda 3$, receiving light thus emitted by the metal complex, and measuring an emission intensity of the light emitted, (iii) a step (hereinafter referred to also as "second irradiation step") for irradiating the metal complex with a light beam having the wavelength $\lambda 2$, (iv) a step (hereinafter referred to also as "second light emission measuring step") for irradiating the metal complex after the second irradiation step with a light beam having the wavelength $\lambda 3$, receiving light thus emitted by the metal complex, and measuring an emission intensity of the light emitted, (v) a step (hereinafter referred to also as "calculating step") for calculating the respective emission intensities measured during the first light emission measuring step and the second light emission measuring step, and (vi) a step (hereinafter referred to also as "identifying step") for identifying identification information associated with a result obtained from the calculating step. There is no particular limit to other details of the method.

The following describes the first irradiation step, the first light emission measuring step, the second irradiation step, the second light emission measuring step, the calculating step, and the identifying step in detail.

(V-1) First Irradiation Step

The first irradiation step involves irradiating the metal complex of the present invention with a light beam of the wavelength $\lambda 1$ to cause the photochromic molecule in the metal complex to change its form from an opened-ring form to a closed-ring form. In the case of using the information identifying medium of the present invention, the information identifying medium is irradiated with a light beam having the wavelength $\lambda 1$ and focused on an information identifying section including the metal complex of the present invention. This operation causes a structural change in the photochromic molecule in the metal complex of the present invention included in the information identifying section of the information identifying medium.

The wavelength $\lambda 1$ is not particularly limited, and is determined in correspondence with the kind of the photochromic molecule. The wavelength $\lambda 1$ preferably falls within an ultraviolet range. Further, there is no particular limit to how to irradiate the metal complex with a light beam of the wavelength $\lambda 1$ during the first irradiation step. The metal complex can be irradiated with such a light beam by a method that uses, for example, a heavy hydrogen lamp, a xenon lamp, a mercury lamp, a halogen lamp, an LED, or a laser.

In addition, there is also no particular limit to how long the metal complex is irradiated with a light beam of the wavelength $\lambda 1$ during the first irradiation step. The metal complex is irradiated with such a light beam for one picosecond or longer, for example.

(V-2) First Light Emission Measuring Step

The first light emission measuring step involves first irradiating the metal complex or information identifying medium after the first irradiation step with a light beam (exciting light) having the wavelength $\lambda 3$. This operation causes the metal complex or information identifying medium to emit light. The first light emission measuring step involves next (i) receiving the light thus emitted and (ii) measuring the intensity of the light emitted.

The wavelength $\lambda 3$ is not particularly limited, and is determined in correspondence with the kind of the metal ion.

Further, there is no particular limit to how to irradiate the metal complex with a light beam of the wavelength λ3 during the first light emission measuring step. The metal complex can be irradiated with such a light beam by a method that uses, for example, a heavy hydrogen lamp, a xenon lamp, a mercury lamp, a halogen lamp, an LED, or a laser.

In addition, there is also no particular limit to how long the metal complex is irradiated with a light beam of the wavelength λ3 during the first light emission measuring step. The metal complex is irradiated with such a light beam for one picosecond or longer, for example.

The first light emission measuring step may involve (i) measuring the intensity of the entire light, emitted by the metal complex, without dispersing it into spectra, (ii) measuring the respective intensities of dispersed emission spectra of the emitted light, or (iii) measuring only the intensity of a line spectrum having a particular wavelength, the line spectrum being among dispersed emission spectra of the emitted light.

In the case where the first light emission measuring step involves measuring the intensity of the entire light emitted by the metal complex, it is possible to (i) simplify an arrangement of a device for measuring the emission intensity and (ii) reduce a period necessary for the first light emission measuring step. In the case where the first light emission measuring step involves measuring the respective intensities of dispersed emission spectra of the emitted light, it is possible to improve accuracy in identifying information. In the case where the first light emission measuring step involves measuring only the intensity of a line spectrum having a particular wavelength, the line spectrum being among dispersed emission spectra of the emitted light, it is possible to (i) simplify an arrangement of a device for measuring the emission intensity, (ii) reduce a period necessary for the first light emission measuring step, and (iii) improve accuracy in identifying information.

The first light emission measuring step in the information identifying method of the present invention preferably involves measuring only the intensity of a line spectrum having a particular wavelength, the line spectrum being among dispersed emission spectra of the light emitted by the metal complex or the information identifying medium. In this case, there is no particular limit to the number of wavelengths to be selected. The number may be one (1), or may be two or more. Increasing the number of wavelengths to be selected can improve accuracy in identifying information. Selecting two wavelengths, for example, makes it possible to (i) calculate a ratio of respective intensities of line spectra of the two wavelengths during the calculating step described below and (ii) identify information on the basis of the ratio during the identifying step described below. Selecting two wavelengths as such thus allows information to be identified with greater accuracy. Further, selecting two wavelengths reduces a time necessary for the first light emission measuring step and the calculating step described below, and consequently reduces a processing time for the information identifying method of the present invention.

There is no particular limit to the above wavelengths to be selected. The wavelengths may simply be selected as appropriate in correspondence with a light emission property of the kind of the metal complex or the information identifying medium in use. The wavelengths to be selected may be, for example, a wavelength of a light beam caused by magnetic dipole transition or electric dipole transition. The present invention particularly preferably selects both of the wavelengths of respective light beams caused by magnetic dipole transition and electric dipole transition. The wavelengths of the respective light beams caused by magnetic dipole transition and electric dipole transition depend on the kind of the metal complex.

The first light emission measuring step may involve measuring, instead of an emission intensity of the metal complex, at least one of a light emission quantum yield and light emission duration of the metal complex for use in the calculating step and the identifying step, or may use a radiation rate constant calculated from the light emission quantum yield and the light emission duration. The first light emission measuring step may alternatively use, duration during the calculating step and the identifying step, a combination of two or more of (i) an emission intensity, (ii) a combination of a plurality of emission intensities, a light emission quantum yield, (iv) a light emission duration, and (v) a radiation rate constant calculated from the light emission quantum yield and the light emission. This operation improves the identification ability.

(V-3) Second Irradiation Step

The second irradiation step involves irradiating the metal complex of the present invention with a light beam of the wavelength λ2 so that the photochromic molecule in the metal complex changes its form from the closed-ring form to the opened-ring form. In the case of using the information identifying medium of the present invention, the information identifying medium is irradiated with a light beam having the wavelength λ2 and focused on an information identifying section including the metal complex of the present invention. This operation causes a structural change in the photochromic molecule in the metal complex of the present invention included in the information identifying section of the information identifying medium.

The wavelength λ2 is not particularly limited, and is determined in correspondence with the kind of the photochromic molecule. The wavelength λ2 preferably falls within a visible range.

There is no particular limit to how to irradiate the metal complex with a light beam of the wavelength λ2 during the second irradiation step. The metal complex can be irradiated with such a light beam by a method that uses, for example, a heavy hydrogen lamp, a xenon lamp, a mercury lamp, a halogen lamp, an LED, or a laser.

In addition, there is also no particular limit to how long the metal complex is irradiated with a light beam of the wavelength λ2 during the second irradiation step. The metal complex is irradiated with such a light beam for one picosecond or longer, for example.

(V-4) Second Light Emission Measuring Step

The second light emission measuring step is identical to the first light emission measuring step, except that the metal complex or information identifying medium after the second irradiation step is irradiated with a light beam (exciting light) having the wavelength λ3. The second light emission measuring step is thus not described here in detail.

(V-5) Calculating Step

The calculating step involves calculating the respective emission intensities measured during the first light emission measuring step and the second light emission measuring step. The calculating step involves, for example, calculating, in the case where the first light emission measuring step and the second light emission measuring step each involve measuring the intensity of the entire light emitted by the metal complex, a ratio of the respective emission intensities.

In the case where the first light emission measuring step and the second light emission measuring step each involve measuring respective intensities of dispersed emission spectra of the light emitted by the metal complex, the calculating step involves (i) calculating (hereinafter referred to also as "first calculating sub-step") a ratio of respective intensities of a plurality of line spectra having particular wavelengths, the respective intensities being among the spectral intensities that have been measured during the first light emission measuring step, and (ii) calculating (hereinafter referred to also as "second calculating sub-step") a ratio of respective intensities of the plurality of line spectra having the particular wavelengths and identical to those mentioned for the first calculating sub-step, the respective intensities being among the spectral intensities that have been measured during the second light emission measuring step. The calculating step may additionally involve calculating (hereinafter referred to also as "third calculating sub-step") a ratio between the ratio calculated during the first calculating sub-step and the ratio calculated during the second calculating sub-step. During the first calculating sub-step and the second calculating sub-step, the number of line spectra to be selected is not particularly limited. The number may be two, or may be three or more. Increasing the number can improve information identification accuracy. Further, the first calculating sub-step and the second calculating sub-step each preferably involve selecting line spectra of respective light beams caused by magnetic dipole transition and electric dipole transition.

In the case where the first light emission measuring step and the second light emission measuring step each involve measuring only the intensity of a line spectrum having a particular wavelength, the line spectrum being among dispersed emission spectra, the calculating step involves calculating a ratio of respective intensities of the line spectra for the first light emission measuring step and the second light emission measuring step. In the case where the first light emission measuring step and the second light emission measuring step each involve measuring respective intensities of a plurality of line spectra having respective wavelengths, the calculating step involves calculating (i) a ratio of the respective intensities of a plurality line spectra, the respective intensities having been measured during the first light emission measuring step, and (ii) a ratio of respective intensities of a plurality of line spectra, the respective intensities having been measured during the second light emission measuring step (the "first calculating sub-step" and the "second calculating sub-step"). The calculating step may additionally involve calculating a ratio of the two ratios thus calculated (the "third calculating sub-step").

Even in the case where the first light emission measuring step and the second light emission measuring step each involve measuring a light emission quantum yield, light emission duration or the like of the metal complex, the calculating step simply involves calculating (i) a ratio of two calculated ratios as with the case of an emission intensity, or (ii) a ratio of two radiation rate constants each calculated from a corresponding light emission quantum yield and a corresponding light emission duration.

(V-6) Identifying Step

The identifying step involves identifying identification information associated with a ratio calculated during the calculating step. Specifically, the identifying step may simply involve identifying identification information associated with a ratio calculated during at least one of the first calculating sub-step, the second calculating sub-step, and the third calculating sub-step. In view of identification accuracy, the identifying step preferably involves identifying identification information associated with ratios calculated during two of the first calculating sub-step, the second calculating sub-step, and the third calculating sub-step, or more preferably identifying identification information associated with ratios of all of the above three sub-steps.

In an embodiment where (i) the first light emission measuring step and the second light emission measuring step each involve measuring the intensity of the entire light emitted by the metal complex and (ii) the calculating step involves calculating a ratio of the respective emission intensities measured during the first light emission measuring step and the second light emission measuring step, the identifying step may simply involve identifying identification information associated with such a ratio.

The above expression "identification information associated with a ratio calculated" refers to the following: Each kind of the metal complex of the present invention has its unique photochromic reactivity and light emission property. Specifically, each kind of the metal complex of the present invention exhibits a unique response to the wavelengths $\lambda 1$, $\lambda 2$, and $\lambda 3$. The ratio calculated during the calculating step is thus a value unique to each kind of the metal complex. This makes it possible to associate the ratio with a metal complex having the ratio. In other words, the expression "identification information associated with a ratio calculated" indicates a metal complex corresponding to the ratio. In the case where a metal complex determined by the ratio calculated is used as a code, any information can be coded with use of such a metal complex. The above identification information thus encompasses any information coded with use of such a metal complex.

The information identifying method of the present invention utilizes both a photochromic property and light emission property of the metal complex of the present invention to (i) determine (identify) a metal complex or a metal complex included in the information identifying medium and to (ii) identify and certify identification information associated with the metal complex. The information identifying method of the present invention thus has an unprecedentedly high identification ability (security).

The information identifying method of the present invention determines a material on the basis of a light intensity, a light intensity ratio, a light emission quantum yield, a light emission quantum yield ratio, a light emission duration, a light emission duration ratio, a radiation rate constant, a radiation rate constant ratio, or a combination thereof. The information identifying method is capable of determining a material even if the metal complex has been degraded. The information identifying method is not restricted by use conditions such as temperature. Further, the metal complex, which is transparent, is normally invisible and thus provides better security. In addition, in the case where a single kind of the metal ion is used, it is possible to recover the metal ion, which is a valuable resource even after its use.

The present invention encompasses an information identifying device including constituent members for carrying out the above respective steps of the information identifying method of the present invention. The information identifying device of the present invention is simply required to include such constituent members that are capable of carrying out the above respective steps. There is no particular limit to details of the arrangement. The information recording and reproduction device of the present invention includes, for example: a light source section for carrying out the first irradiation step; a light source section, light receiving section, and emission intensity calculating section each for carrying out the first light emission measuring step; a light source section for carrying out the second irradiation step; a light source section, light receiving section, and emission intensity calculating section each for carrying out the second light emission measuring step; an emission intensity analyzing section for carrying out the calculating step; and an identifying section for carrying out the identifying step.

The present invention is not limited to the description of the arrangements above, but may be altered in various ways by a skilled person within the scope of the claims. Any embodiment based on a proper combination of technical means disclosed in different embodiments is also encompassed in the technical scope of the present invention.

Example 1

The following describes the present invention with reference to Examples in detail. The present invention is, however, not limited to the descriptions thereof.

Example 1

Synthesis of Tris(hexafluoroacetylacetonato) [1,2-bis (2-methyl-1-benzothiophene-1,1-dioxide-3-yl) perfluorocyclopentene]europium(III) (Hereinafter Referred to as [Eu(BTFO4)(HFA)$_3$] as Appropriate)]

[Eu(HFA)$_3$(H$_2$O)$_2$] was reacted with 1,2-bis(2-methyl-1-benzothiophene-1,1 dioxide-3-yl) perfluorocyclopentene (BTFO4) to synthesize Eu(III) complex [Eu(BTFO4)(HFA)$_3$]. The BTFO4 was synthesized by a method described in Jeong, Y. C.; Yang, S. I.; Ahn, K. H.; Kim, E. Chem. Commun. 2005, 2503-2505.

First, [Eu(HFA)$_3$(H$_2$O)$_2$] (60 mg, 0.11 mmol) and 1,2-bis (2-methyl-1-benzothiophene-1,1-dioxide-3-yl) perfluorocyclopentene (hereinafter referred to as "BTFO4" as appropriate) (90 mg, 0.11 mmol) were dissolved in a mixed solution of methanol (10 ml) and chloroform (5 ml). The resultant solution was refluxed while heated for one (1) day for reaction. After the reaction was stopped, a solvent was evaporated from the reaction solution. The resultant product was washed with chloroform and hot hexane several times to afford a colorless powder (amount of yield: 80 mg, rate of yield: 56%).

The above-obtained colorless powder was subjected to a $^1$H-NMR measurement, an IR measurement, and an ESI-Mass measurement, to determine that the colorless powder was [Eu(BTFO4)(HFA)$_3$]. $^1$H-NMR (300 MHz, CDCl$_3$) δ=2.13 (s, 3H), 2.30 (s, 3H), 7.22 (d, 2H), 7.48 (m, 2H), 7.62 (m, 2H), 7.80 (m, 2H). IR=3300 w, 2929 m, 2852 m, 1648 s, 1535 s, 1461 s, 1251 s, 1203 s, 1139 s cm$^{-1}$. ESI mass spectrum (m/z) calculated value for [M]$^+$ C$_{33}$, H$_{16}$, EuF$_{18}$, O$_8$, S$_2$: 1098.92; and found value: 1098.92.

The $^1$H-NMR measurement was made on a JEOL AL-300 spectrometer (300 MHz), and the $^1$H-NMR chemical shift was determined with reference to tetramethylsilane (TMS) as an internal standard. The IR measurement was made on a JASCO FT/IR-420 spectrometer. The ESI-Mass measurement was made with use of JEOL JMS-700 Mstation.

Example 2

Light Emission Property of [Eu(BTFO4)(HFA)$_3$]

A comparison was made for a light emission property between [Eu(BTFO4)(HFA)$_3$] in which an opened-ring ligand (BTFO4-0) was coordinated and [Eu(BTFO4)(HFA)$_3$] in which a closed-ring ligand (BTFO4-C) was coordinated.

First, the [Eu(BTFO4)(HFA)$_3$] in which a closed-ring ligand (BTFO4-C) was coordinated was prepared by separating a closed-ring ligand (BTFO4-C) from a colored BTFO4 solution by HPLC and reacting the closed-ring ligand (BTFO4-C) with [Eu(HFA)$_3$(H$_2$O)$_2$] as in Example 1.

[Eu(BTFO4)(HFA)$_3$] in an ethyl acetate solution (1.6× 10$^{-5}$ M) of the above-prepared [Eu(BTFO4)(HFA)$_3$] in which the closed-ring ligand (BTFO4-C) was coordinated was excited by exciting light of a wavelength of 526 nm to measure an emission spectrum on a JASCO FP-6500 spectrometer.

FIG. 1 shows a solid line indicative of the emission spectrum due to the 526 nm excitation (f-f transition) of the [Eu(BTFO4)(HFA)$_3$], in which the closed-ring ligand (BTFO4-C) was coordinated, in the ethyl acetate solution. The emission spectrum was observed to have light emissions due to the f-f transitions at 578 nm ($^5$D$_0$-$^7$F$_0$), 592 nm ($^5$D$_0$-$^7$F$_1$), 615 nm ($^5$D$_0$-$^7$F$_2$), 650 nm ($^5$D$_0$-$^7$F$_3$), and 698 nm ($^5$D$_0$-$^7$F$_4$). The ethyl acetate solution was irradiated with visible light (800 nm>λ>420 nm), so that the [Eu(BTFO4) (HFA)$_3$] had an increased emission intensity due to the irradiation of the visible light, as indicated by a broken line in FIG. 1.

This was because, as illustrated in the following Formula (8):

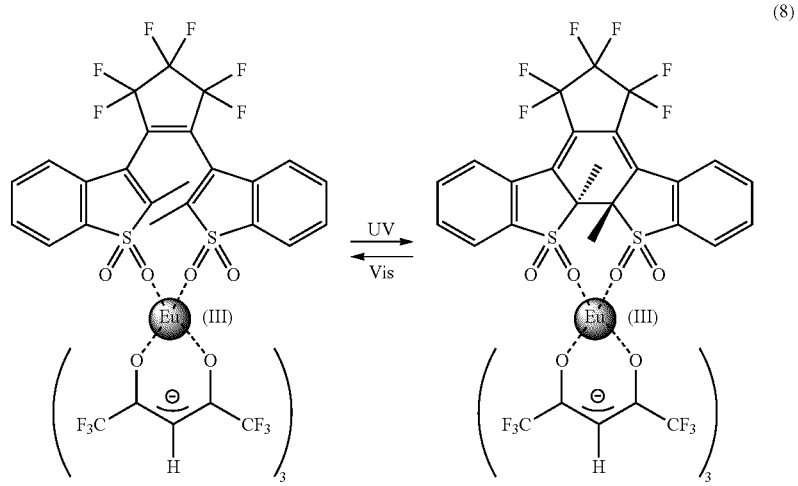

(8)

the irradiation of the visible light (indicated by "Vis" in Formula (8)) changed the $[Eu(BTFO4)(HFA)_3]$ in which the closed-ring ligand (BTFO4-C) was coordinated into $[Eu(BTFO4)(HFA)_3]$ in which an opened-ring ligand (BTFO4-O) was coordinated. The above visible light was light of [800 nm>λ>420 nm] obtained by passing light through a colored glass filter (SCF-50S-42L, available from SIGMA KOKI).

Figure 2:
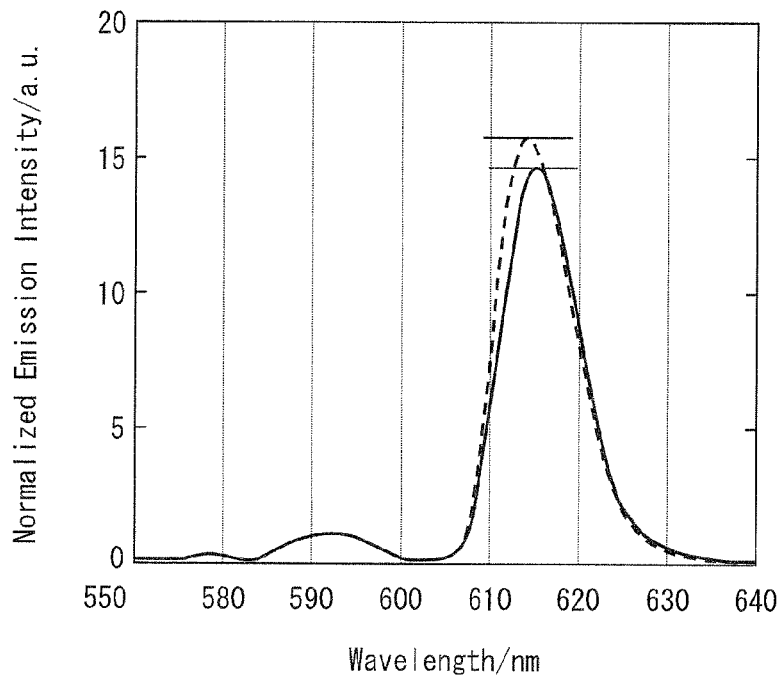
FIG. 2 is a graph in which an emission intensity at 592 nm of an emission spectrum of [Eu(BTFO4)(HFA)$_3$] is standardized as 1, in accordance with an embodiment of the present invention.

The light emission at 592 nm ($^5D_0$-$^7F_1$) is due to magnetic dipole transition, which is known to not depend on the coordination environment (symmetry of the complex) around the Eu(III) ion. The light emission at 615 nm ($^5D_0$-$^7F_2$), in contrast, is due to electric dipole transition, and greatly changes depending on symmetry of the complex. Thus, the coordination environment of a Eu(III) ion can be evaluated on the basis of a change in intensity of a light emission caused by electric dipole transition, the change being relative to a change in intensity of a light emission caused by magnetic dipole transition. In view of this, to study an emission intensity change in detail, the observed emission spectrum was standardized so that the emission intensity at 592 nm (that is, the light emission due to magnetic dipole transition: $^5D_0$-$^7F_1$) was 1. The standardization made it clear that a relative emission intensity at 615 nm (that is, the light emission due to electric dipole transition: $^5D_0$-$^7F_2$) is increased due to irradiation of visible light as illustrated in FIG. 2.

The above observation indicates that the emission intensity of the metal complex of the present invention highly sensitively changes due to a change in the molecular structure caused by a photochromic reaction of the ligand.

As described below, the emission spectrum and absorption spectrum of $[Eu(BTFO4)(HFA)_3]$ in which (BTFO4) is an opened-ring form do not coincide with those of (BTFO4)(HFA)$_3$] in which (BTFO4) is a closed-ring form. Thus, the change in the emission intensity at 615 nm cannot be due to optical switching caused by a resonance energy transfer. The above increase in the emission intensity of $[Eu(BTFO4)(HFA)_3]$ caused by irradiation of visible light is probably because the irradiation of visible light changes the molecular structure of the photochromic molecule to consequently change the coordination structure of the complex. The probability that the increase is due to a change in coordination structure caused by a photochromic reaction is further supported by the fact that a maximum wavelength of the light emission due to electric dipole transition changes after light irradiation.

Example 3

Photochromic Property of $[Eu(BTFO4)(HFA)_3]$

Figure 3:
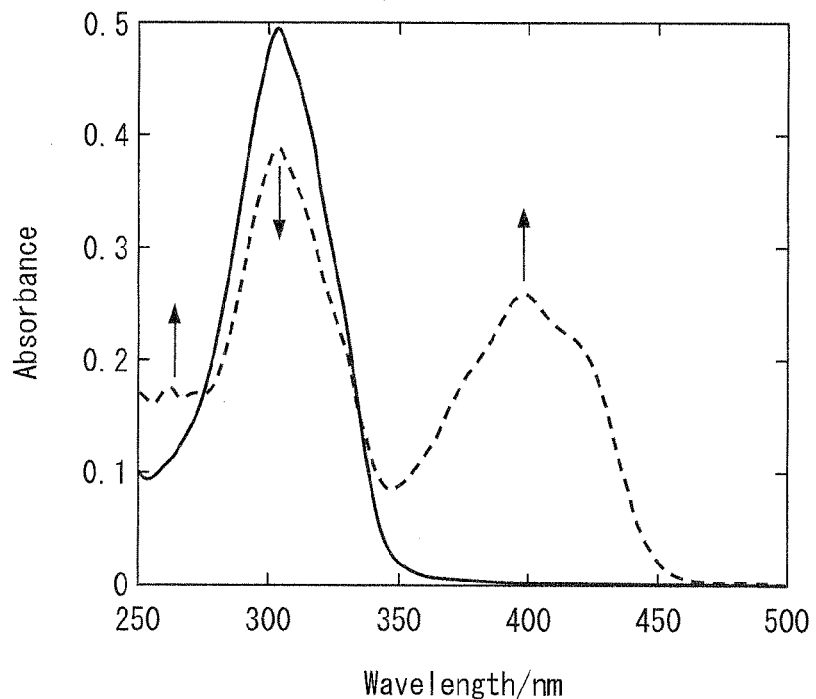
FIG. 3 is a graph indicative of an absorption spectrum of [Eu(BTFO4)(HFA)$_3$] in accordance with an embodiment of the present invention.

Measurements were made, with use of JASCO V-550, of an absorption spectrum of $[Eu(BTFO4)(HFA)_3]$, in which the opened-ring ligand (BTFO4-O) obtained in Example 1 was coordinated, in an ethyl acetate solution ($1.6\times10^{-5}$M). FIG. 3 shows a solid line indicative of the absorption spectrum thus measured.

Next, the ethyl acetate solution of $[E(BTFO4)(HFA)_3]$ was irradiated with ultraviolet light of 313 nm. The ultraviolet light for irradiation was monochromatic light of 313 nm obtained by passing light through a monochromator (SPG120-S, available from Shimadzu). The above irradiation caused a new absorption band to appear at 398 nm within the visible range as indicated by a broken line of FIG. 3. The absorption spectrum change had an isosbestic point at 334 nm. A color change from colorless to yellow was observed even visually.

After being colored, the ethyl acetate solution was irradiated with visible light (800 nm>λ>420 nm), so that the absorption band at and around 398 nm disappeared and an absorption at and around 304 nm was recovered. The above visible light was light of [800 nm>λ>420 nm] obtained by passing light through a colored glass filter (SCF-50S-42L, available from SIGMA KOKI).

The ethyl acetate solution was irradiated again with ultraviolet light after the above operation, so that the absorption band at and around 398 nm reappeared. This indicates that the above optical reaction is a reversible photochemical reaction. Further, a verification was made that the coloration reaction and bleaching reaction can be repeated 10 or more times.

Example 4

Light Emission Property of $[Eu(BTFO4)(HFA)_3]$ Observed when $[Eu(BTFO4)(HFA)_3]$ is Continuously Irradiated with Exciting Light]

Figure 4:
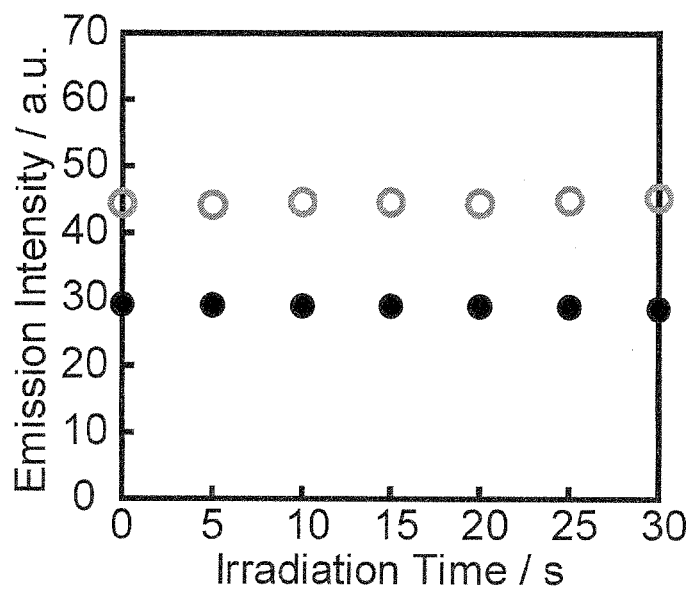
FIG. 4 is a graph indicative of respective emission intensities at 615 nm of (i) [Eu(BTFO4)(HFA)$_3$] in which an opened-ring ligand (BTFO4-O) is coordinated and (ii) [Eu(BTFO4)(HFA)$_3$] in which a closed-ring ligand (BTFO4-C) is coordinated, the emission intensities being observed when [Eu(BTFO4)(HFA)$_3$] of an embodiment of the present invention is continuously irradiated with exciting light of 526 nm.

Measurements were made for a time-dependent change in light emission property by continuously irradiating, with exciting light of 526 nm, $[Eu(BTFO4)(HFA)_3]$ in which an opened-ring ligand (BTFO4-O) was coordinated and $[Eu(BTFO4)(HFA)_3]$ in which a closed-ring ligand (BTFO4-C) was coordinated. FIG. 4 illustrates a temporal change in emission intensity at 615 nm. FIG. 4 illustrates (i) white circles indicative of results for the $[Eu(BTFO4)(HFA)_3]$ in which an opened-ring ligand (BTFO4-O) was coordinated and (ii) black circles indicative of results for the $[Eu(BTFO4)(HFA)_3]$ in which a closed-ring ligand (BTFO4-C) was coordinated. The above measurements showed, as is clear from FIG. 4, that continuous irradiation of exciting light causes no change in the emission intensity or emission spectrum of the $[Eu(BTFO4)(HFA)_3]$ in which an opened-ring ligand (BTFO4-O) was coordinated or of the $[Eu(BTFO4)(HFA)_3]$ in which a closed-ring ligand (BTFO4-C) was coordinated. The measurements further indicate that with $[Eu(BTFO4)(HFA)_3]$, it is possible to read out an emission intensity change in a nondestructive manner with use of exciting light of 526 nm.

Example 5

Light Emission Quantum Yield ($\Phi_{emi}$), Light Emission Duration ($\tau_{emi}$), and Radiation Rate Constant ($k_r$) of $[Eu(BTFO4)(HFA)_3]$ A kinetic analysis was made to find further details of the emission intensity change observed in the $[Eu(BTFO4)(HFA)_3]$.

Specifically, measurements were made for a light emission quantum yield ($\Phi_{emi}$) and light emission duration ($\tau_{emi}$) of $[Eu(BTFO4)(HFA)_3]$ in which an opened-ring ligand (BTFO4-O) was coordinated and $[Eu(BTFO4)(HFA)_3]$ in which a closed-ring ligand (BTFO4-C) was coordinated. Further, a radiation rate constant ($k_r$) for each of them was calculated from the above Formulae (1) and (2).

The light emission duration was measured by exciting $[Eu(BTFO4)(HFA)_3]$ at room temperature with use of Nd-YAG laser (INDI, available from Spectra Physics) and detecting a light emission with use of a photomultiplier (Photomultiplier R5108, available from Hamamatsu Photonics). The emission spectra were measured with use of FP-6600, available from JASCO Corporation. The measurements involved an ethyl acetate solution of $[Eu(BTFO4)(HFA)_3]$ having a concentration of $1.6\times10^{-5}$M.

The light emission quantum yield of [Eu(BTFO4)(HFA)$_3$] at room temperature was calculated by a relative method with use of [Eu(HFA)$_3$BIPHEPO] (Φ=0.60) as a reference compound. Specifically, first, [Eu(HFA)$_3$BIPHEPO] (acetone solution, 1.0×10$^{-3}$M) and [Eu(BTFO4)(HFA)$_3$] (ethyl acetate solution, 1.0×10$^{-3}$M) were prepared. Then, absorption spectra of the respective solutions were measured. The light emission quantum yield was calculated with reference to a peak that is due to Eu, which has a peak top at 465 nm, and that is so low as to hardly appear in FIG. 3. The light emission quantum yield was calculated by using, as an absorption area ($A_{abs}$), an area of the peak with its peak top at 465 nm. Further, measurements were made of emission spectra for the respective complexes to calculate a light emission area ($A_{emi}$).

The light emission quantum yield ($\Phi_{emi}$) was calculated from the above-calculated values by the following formula:

$$\Phi_{emi} = \Phi_{ref} \times (A_{emi}/A_{emi-r}) \times (A_{abs-r}/A_{abs}) \times (n_{ethyl\ acetate}/n_{acetone})^2.$$

In the formula above, the symbols represent the values specified below.

$\Phi_{emi}$=light emission quantum yield of [Eu(BTFO4)(HFA)$_3$]
$\Phi_{ref}$=light emission quantum yield of [Eu(HFA)$_3$BIPHEPO]
$A_{emi}$=light emission area of [Eu(BTFO4)(HFA)$_3$]
$A_{emi-r}$=light emission area of [Eu(HFA)$_3$BIPHEPO]
$A_{abs-r}$=absorption area of [Eu(HFA)$_3$BIPHEPO]
$A_{abs}$=absorption area of [Eu(BTFO4)(HFA)$_3$]
$n_{ethyl\ acetate}$=refractive index of ethyl acetate
$n_{acetone}$=refractive index of acetone Table 1 shows the light emission quantum yield ($\Phi_{emi}$), light emission duration ($\tau_{emi}$) and radiation rate constant ($k_r$) of each of [Eu(BTFO4)(HFA)$_3$] in which an opened-ring ligand (BTFO4-O) was coordinated and [Eu(BTFO4)(HFA)$_3$] in which a closed-ring ligand (BTFO4-C) was coordinated.

TABLE 1

| | $\Phi_{emi}$ | $\tau_{emi}$ (ms) | $k_r$ ($10^2 s^{-1}$) |
|---|---|---|---|
| [Eu(BTFO4)(HFA)$_3$] in which an opened-ring ligand (BTFO4-O) is coordinated | 0.16 | 0.71 | 2.3 |
| [Eu(BTFO4)(HFA)$_3$] in which a closed-ring ligand (BTFO4-C) is coordinated | 0.10 | 0.68 | 1.5 |

As shown in Table 1, the radiation rate constant of the [Eu(BTFO4)(HFA)$_3$] in which an opened-ring ligand (BTFO4-O) was coordinated was 1.5 times as large as that of the [Eu(BTFO4)(HFA)$_3$] in which a closed-ring ligand (BTFO4-C) was coordinated. This is probably because admissibility of transition of the [Eu(BTFO4)(HFA)$_3$] in which an opened-ring ligand (BTFO4-O) was coordinated has been increased over the [Eu(BTFO4)(HFA)$_3$] in which a closed-ring ligand (BTFO4-C) was coordinated. This probability is supported by the fact that electric dipole transition at 615 nm in the emission spectrum change is larger in the [Eu(BTFO4)(HFA)$_3$] in which an opened-ring ligand (BTFO4-O) was coordinated.

The above results show that information or a code stored in the photochromic molecule can be read out not only by measuring an emission intensity, but also by a simple method of measuring a light emission quantum yield and/or light emission duration.

Making the above numerical analysis (that is, a radiation rate analysis) of values obtained by measuring a light emission quantum yield and a light emission duration makes it possible to encode, in the form of a value, information or a code stored in the photochromic molecule.

Since the method for decoding information or a code stored in the photochromic molecule can be extended and numerized as above, it is possible to improve security for the information and code. In other words, since the method for decoding the information or code can be based on any of an emission intensity, a light emission quantum yield, a light emission duration, a radiation rate constant, and a combination thereof, it is possible to improve security.

Example 6

Synthesis of Tris(hexafluoroacetylacetonato) [1,2-bis (2-methyl-1-benzothiophene-1,1-dioxide-3-yl) perfluorocyclopentene] Neodymium (III) (Hereinafter Referred to as [Nd(BTFO4)(HFA)$_3$] as Appropriate)

[Nd(HFA)$_3$(H$_2$O)$_2$] was reacted with BTFO4 to synthesize Nd(III) complex [Nd(BTFO4)(HFA)$_3$].

First, a chloroform solution (100 ml) of BTFO4 (0.29 g, 0.55 mmol) was added to a methanol solution (150 ml) of [Nd(HFA)$_3$(H$_2$O)$_2$] (0.48 g, 0.60 mmol). The resultant solution was refluxed while heated for one (1) day for reaction. After the reaction was stopped, a solvent was evaporated from the reaction solution. The resultant product was washed with chloroform and hot hexane several times to afford a colorless powder (amount of yield: 0.23 g, rate of yield: 32%).

The above-obtained colorless powder was subjected to a $^1$H-NMR measurement and an ESI-Mass measurement, to determine that the colorless powder was [Nd(BTFO4)(HFA)$_3$]. $^1$H-NMR (300 MHz, CDCl$_3$) δ=2.03 (s, 3H), 2.16 (s, 3H), 7.15 (m, 2H), 7.44 (m, 2H), 7.59 (m, 2H), 7.70 (m, 2H) ppm. ESI mass spectrum (m/z) calculated value for [M]+ C$_{33}$, H$_{16}$, NdF$_{18}$, O$_8$, S$_2$: 1087; and measured value: 1087. The $^1$H-NMR measurement and the ESI-Mass measurement were made in the same manner as in Example 1.

Figure 10:
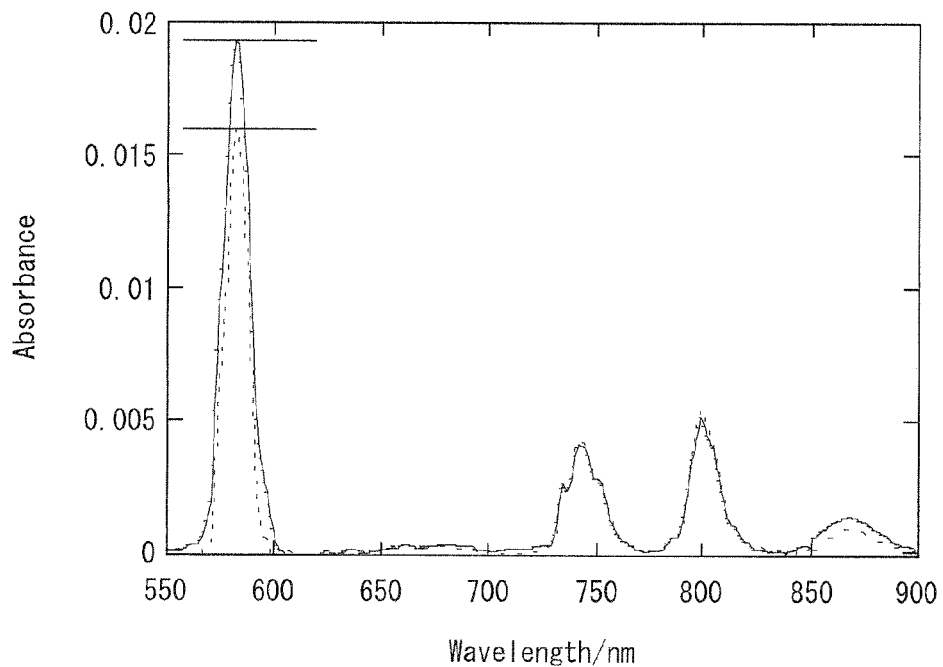
FIG. 10 is a graph illustrating an absorption spectrum caused by a Nd(III) ion in [Nd(BTFO4)(HFA)$_3$] in accordance with an embodiment of the present invention.

FIG. 10 shows respective absorption spectra of (i) [Nd(BTFO4)(HFA)$_3$] in which an opened-ring ligand (BTFO4-O) was coordinated and (ii) [Nd(BTFO4)(HFA)$_3$] in which a closed-ring ligand (BTFO4-C) was coordinated, both in an acetone solution (3.0×10$^{-3}$M). The absorption spectra shown in FIG. 10 are due to the Nd(III) ion of [Nd(BTFO4)(HFA)$_3$]. Respective absorption bands of (BTFO4-0) and (BTFO4-C) of [Nd(BTFO4)(HFA)$_3$], which absorption bands are present at shorter wavelengths, are not shown in FIG. 10, but are identical to those shown in FIG. 3. FIG. 10 shows (i) a solid line indicative of an absorption spectrum of the [Nd(BTFO4)(HFA)$_3$] in which an opened-ring ligand (BTFO4-O) was coordinated and (ii) a dotted line indicative of an absorption spectrum of the [Nd(BTFO4)(HFA)$_3$] in which a closed-ring ligand (BTFO4-C) was coordinated, that is, a colored body after light irradiation.

FIG. 10 indicates that in [Nd(BTFO4)(HFA)$_3$], an absorption band (write, erase) caused by the photochromic molecule does not coincide with an absorption band caused by the Nd(III) ion. Absorption at and around 582 nm due to the Nd(III) ion changes in correspondence with a structural change in the photochromic molecule. These results demonstrate that identifying a change in absorption at and around 582 nm makes it possible to read out, in a nondestructive manner, information that has been written to or erased from the photochromic molecule.

INDUSTRIAL APPLICABILITY

The metal complex of the present invention, which has the above arrangement, is characterized by a property of the metal ion for a light emission due to a structural change in the ligand, particularly a high emission intensity of the metal ion and a significantly large change in the emission intensity.

Further, in the metal complex of the present invention, an absorption band (write, erase) caused by the photochromic molecule differs from an absorption band of the metal complex, that is, a wavelength (readout) of exciting light and an emission wavelength (memory detection) of the metal complex. This makes it possible to read out optically stored information in a nondestructive manner.

The metal complex of the present invention is thus usable as, for example, an information storage medium, a non-volatile memory, and a switching element. Further, the photochromic molecule is characterized by the capability to record optical information for each molecule. The metal complex of the present invention is therefore a new material that is highly useful for the information-oriented society.

The invention claimed is:

1. A metal complex having a structure represented by General Formula (7) below,

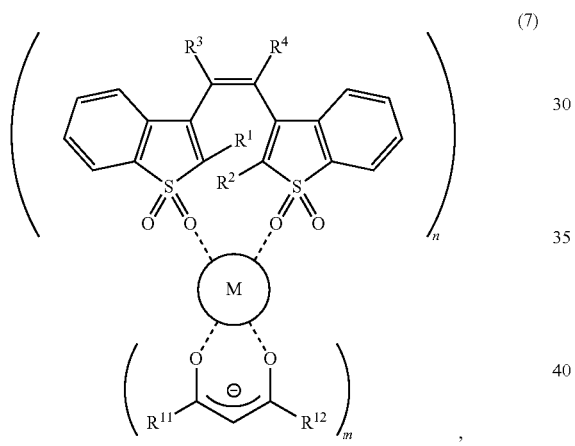

where:

$R^1$ and $R^2$ are each independently an alkyl group;

$R^3$ and $R^4$ together form a substituted or unsubstituted five-membered hydrocarbon ring;

$R^{11}$ and $R^{12}$ are each independently an alkyl group having 1 to 8 carbon atoms, or a fluorine-substituted alkyl group having 1 to 8 carbon atoms;

M represents a metal ion;

n is 1; and m is 3.

2. The metal complex according to claim 1,
wherein the metal ion is a rare-earth ion.

3. The metal complex according to claim 2,
wherein the rare-earth ion is a trivalent ion.

4. The metal complex according to claim 3,
wherein the trivalent ion is selected from the group consisting of $Ce^{3+}$, $Nd^{3+}$, $Sm^{3+}$, $Eu^{3+}$, $Tb^{3+}$, $Dy^{3+}$, $Er^{3+}$, $Pr^{3+}$, $Tm^{3+}$, and $Yb^{3+}$.

5. A composition, comprising:
the metal complex according claim 1; and
an organic solvent, a resin, an inorganic material, or an organic-inorganic hybrid material.

6. The metal complex according to claim 1,
wherein $R^1$ and $R^2$ are each independently a linear or branched alkyl group having 1 to 20 carbon atoms.

7. The metal complex according to claim 1,
wherein $R^{11}$ and $R^{12}$ are each independently a fluorine-substituted alkyl group having 1 to 8 carbon atoms.

* * * * *